United States Patent
Ueno et al.

(10) Patent No.: US 6,600,558 B2
(45) Date of Patent: Jul. 29, 2003

(54) MICRO-FLUIDIC CELL FOR OPTICAL DETECTION OF GASES AND METHOD FOR PRODUCING SAME

(75) Inventors: Yuko Ueno, Tama (JP); Tsutomu Horiuchi, Atsugi (JP); Takashi Morimoto, Kawasaki (JP); Osamu Niwa, Atsugi (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 0 days.

(21) Appl. No.: 09/934,286

(22) Filed: Aug. 21, 2001

(65) Prior Publication Data

US 2002/0024662 A1 Feb. 28, 2002

(30) Foreign Application Priority Data

Aug. 22, 2000 (JP) .......................................... 2000-251126
May 2, 2001 (JP) .......................................... 2001-135152

(51) Int. Cl.$^7$ ................................................. G01N 1/10
(52) U.S. Cl. ..................... 356/246; 356/244; 422/82.09; 422/102
(58) Field of Search ................................. 356/244, 246, 356/454; 422/58, 82.05, 82.09, 102, 68.1; 385/12, 31, 89

(56) References Cited

U.S. PATENT DOCUMENTS

| | | | | |
|---|---|---|---|---|
| 5,311,274 A | * | 5/1994 | Cole, Jr. ...................... | 356/133 |
| 5,589,136 A | * | 12/1996 | Northrup et al. ........ | 422/82.09 |
| 6,020,207 A | * | 2/2000 | Liu ......................... | 422/82.08 |
| 6,341,185 B1 | * | 1/2002 | Elster et al. ................ | 356/454 |
| 6,350,413 B1 | * | 2/2002 | Reichert et al. ......... | 422/82.11 |
| 6,379,929 B1 | * | 4/2002 | Burns et al. ................ | 436/501 |
| 6,444,474 B1 | * | 9/2002 | Thomas et al. ............... | 422/58 |

FOREIGN PATENT DOCUMENTS

| | | | |
|---|---|---|---|
| JP | 2000241313 A | | 8/2000 |
| JP | 2000241314 A | | 8/2000 |
| WO | WO-02/061400 | * | 1/2001 |

\* cited by examiner

Primary Examiner—Frank G. Font
Assistant Examiner—Sang H. Nguyen
(74) Attorney, Agent, or Firm—Workman, Nydegger & Seeley

(57) ABSTRACT

A micro-fluidic cell for optical detection of gases provided according to the present invention includes a concentration cell and a detection cell, and increases the sensitivity of optical detection of gases, selectivity of components, and accuracy of quantitative determination, and also achieves a low electric power consumption and a small-sized, light-weight configuration of the entire apparatus.

35 Claims, 16 Drawing Sheets

MICRO-FLUIDIC CELL FOR OPTICAL DETECTION OF GASES AND METHOD FOR PRODUCING SAME

This application is based on Japanese Patent Application Nos. 2000-251126 filed Aug. 22, 2000 and 2001-135152 filed May 2, 2001 the content of which is incorporated hereinto by reference.

BACKGROUND OF THE INVENTION

1. Field of the Invention

This invention relates to a micro-fluidic cell for optical detection of gases for use in a sensor for detecting trace substances present in the air, a method for producing the micro-fluidic cell for optical detection of gases, and a gas trapping cell for use in the micro-fluidic cell for optical detection of gases. The present invention also relates to an apparatus for optical detection of gases which is equipped with the micro-fluidic cell for optical detection of gases.

2. Description of the Related Art

For analysis of organic gases causing air pollution, the concentrations of the gases to be analyzed (may hereinafter referred to as target gases) are generally very low. Thus, gas trapping treatment of the low concentration target gases is necessary at a stage prior to the analysis operation. Conventional concentration and analysis devices most widely use a device for adsorbing target gases to an adsorbent loaded in an adsorbing collection tube, and then applying thermal desorption treatment to recover the target gases as concentrated gases with high concentrations, and introducing these gases into the analyzer.

The procedure for use, and the problems with, the conventional concentration and analysis devices will be briefly described below, with a gas analyzer comprising a combination of analysis means, such as an ultraviolet (UV) spectrophotometer (Japanese Patent Application Laying-open No. 2000-241313), and a method comprising gas chromatography and cold trapping, being taken as examples.

At a site for which analysis should be made, the air containing organic target gases is introduced into a collection tube, and the gases are collected into the adsorbent. Then, the collection tube is heated to desorb the organic gases adsorbed to the adsorbent as concentrated gases. Then, the concentrated gases are introduced into an analyzer, such as an ultraviolet spectrophotometer, if it is used as means for analysis. If a gas chromatograph is used as means of analysis, the concentrated gases are recovered again into a cold trap device in which liquid nitrogen is circulated, whereafter the concentrated gases are reheated quickly, and introduced into the gas chromatographic analyzer.

In these procedures, the following problems arise: The collection tube so far used has dimensions as large as several millimeters in diameter and several tens of centimeters in length. Thus, when the gases are recovered by desorption upon heating, the adsorbent is heated uniformly, and the recovery by desorption does not give a sharp response. As a result, the concentration effect declines, and sensitivity lowers. The thickness of the tube wall is as large as 1 mm or more, so that when the outer wall is heated with the heater, a temperature difference occurs between the heater and the adsorbent loaded in the tube, decreasing temperature control accuracy. When the heating temperature of the adsorbent is controlled to an appropriate desorption temperature in each target gases to separate them into components, the large volume of the collection tube decreases the accuracy of temperature control, thus leading to poor separation into the components. When the heating portion is large, a high heating temperature and a long heating time need to be set in order to heat the entire adsorbent to a temperature necessary for desorption of the gases. Hence, the problem of an increased electric power consumption is also caused.

Moreover, the internal diameter of the collection tube is as large as about several millimeters. Thus, there is need to put quartz wool, rid of interfering components, ahead of and behind the adsorbent to set the adsorbent in place. When a powdery adsorbent is used, the adsorbent enters between the fibers of the quartz wool, varying the cross section area of contact between the adsorbent and the gases. This may cause a decrease in the measurement accuracy.

Furthermore, when the concentrated gases are introduced into the analyzer such as an ultraviolet spectrophotometer, the concentrated gases diffuse in the detection cell, if the inner volume of the detection cell is as large as about several tens of cubic centimeters relative to the optical path length of 10 cm. As a result, the concentration effect declines, and the sensitivity lowers. The large size of the detection cell also poses the problem that the concentration of the gas becomes different between the wall surface and the center of the cell, causing an error of quantitative measurement.

Besides, when the concentrated gases are recovered into the cold trap device, the high temperature gases are cooled and recovered as described above. Thus, the cold trap device needs to be cooled by circulation of a refrigerant such as liquid nitrogen. For this purpose, a refrigerant reservoir with a capacity of about 10 liters, and a refrigerant circulator are required, making the scale of the apparatus large. The cold trap device solidifies the gases to recover them. The gases need to be reheated for recover, thus requiring an additional form of heating system.

SUMMARY OF THE INVENTION

The present invention has been accomplished in consideration of the above circumstances. It is an object of the invention to provide a micro-fluidic cell for optical detection of gases comprising a concentration cell and a detection cell, and a method for producing the micro-fluidic cell for optical detection of gases in order to increase the sensitivity of optical detection of gases, selectivity of components, and accuracy of quantitative determination, and also achieve a low electric power consumption and a small-sized, lightweight configuration of the entire apparatus. It is another object of the invention to provide a gas trapping cell including a cold trap channel as the concentration cell. It is a further object of the invention to provide a gas analyzer having a micro-fluidic cell for optical detection of gases.

In a first aspect of the present invention, there is provided a micro-fluidic cell for optical detection of gases comprising:

a microchannel through which gases to be analyzed flow;

a concentration cell; and a detection cell, and wherein the microchannel through which gases to be analyzed flow comprises a first microchannel including a gas inlet, a second microchannel including a gas outlet, and a connecting channel which connects the first microchannel and the second microchannel, the concentration cell has the first microchannel, a substance adapted to adsorb and desorb the gases to be analyzed, and provided in part of the first microchannel, and a heating source for heating the substance for adsorbing and desorbing the gases to be analyzed, and the detection cell has the second microchannel, an optical fiber for entry of ultraviolet light for spectrophotometric analysis into the second microchannel, and an optical fiber for exit of the ultraviolet light for spectrophotometric analysis from the second microchannel.

In a second aspect of the present invention, there is provided a gas trapping cell comprising:

a microchannel having a gas inlet and a gas outlet port and permitting flow of gases to be analyzed;

a substance provided in part of the microchannel and adapted to adsorb and desorb the gases to be analyzed;

a heating source for heating the substance for adsorbing and desorbing the gases to be analyzed; and a microchannel for cold-trapping the gases to be analyzed which have been desorbed from the substance for adsorption and desorption provided in part of the microchannel.

In a third aspect of the present invention, there is provided a method for producing a micro-fluidic cell for optical detection of gases, comprising the steps of:

forming a trench in a continuous pattern including an adsorbent stopper step on a top side of a first substrate;

loading a substance for adsorbing and desorbing gases into part of the trench;

connecting an optical fiber for entry of ultraviolet light for spectrophotometric analysis and an optical fiber for exit of the ultraviolet light for spectrophotometric analysis with a predetermined spacing in the trench by use of an sealing material comprising glass;

bonding a second flat substrate to the top side of the first substrate by bonding to form a microchannel in the trench; and providing a heater on a bottom side of the first substrate and at a position corresponding to a portion loaded with the substance for adsorbing and desorbing the gases.

In a fourth aspect of the present invention, there is provided a method for producing a micro-fluidic cell for optical detection of gases, comprising the steps of:

forming a trench in a continuous pattern including an adsorbent stopper step on a top side of a first substrate;

loading a substance for adsorbing and desorbing gases into part of the trench;

forming a trench in a predetermined continuous pattern on a top side of a second substrate and a through-hole in the trench;

connecting an optical fiber for entry of ultraviolet light for spectrophotometric analysis and an optical fiber for exit of the ultraviolet light for spectrophotometric analysis with a predetermined spacing in the trench of the second substrate by use of an sealing material comprising glass;

bonding a third flat substrate to the top side of the second substrate by bonding to form a microchannel in the trench of the second substrate;

bonding a bottom side of the second substrate to the top side of the first substrate by bonding to form a microchannel in the trench of the first substrate; and providing a heater on a bottom side of the first substrate and at a position corresponding to a portion loaded with the substance for adsorbing and desorbing the gases.

In a fifth aspect of the present invention, there is provided a method for producing a micro-fluidic cell for optical detection of gases, comprising the steps of:

forming a trench in a continuous pattern including an adsorbent stopper step on a top side of a first substrate;

loading a substance for adsorbing and desorbing gases into part of the trench;

bonding a second flat substrate having a through-hole at a position corresponding to the trench of the first substrate to the top side of the first substrate by bonding to form a microchannel in the trench of the first substrate;

providing a heater on a bottom side of the first substrate and at a position corresponding to a portion loaded with the substance for adsorbing and desorbing the gases;

forming a trench in a predetermined continuous pattern on a top side of a third substrate and a through-hole in the trench;

connecting an optical fiber for entry of ultraviolet light for spectrophotometric analysis and an optical fiber for exit of the ultraviolet light for spectrophotometric analysis with a predetermined spacing in the trench of the third substrate by use of an sealing material comprising glass;

bonding a fourth flat substrate having a through-hole at a position corresponding to the trench of the third substrate to the top side of the third substrate by bonding to form a microchannel in the trench of the third substrate; and stacking a fifth substrate comprising a Teflon seal packing interposed between the second substrate and the third substrate and having a through-hole at a position corresponding to the through-hole of the second substrate and the through-hole of the fourth substrate.

In a sixth aspect of the present invention, there is provided an apparatus for optical detection of gases, comprising:

a micro-fluidic cell for optical detection of gases, including a microchannel through which gases to be analyzed flow, a concentration cell, and a detection cell;

a heater power source;

an ultraviolet light source;

an ultraviolet spectrophotometer; and a controller, and wherein the microchannel through which the gases to be analyzed flow comprises a first microchannel including a gas inlet, a second microchannel including a gas outlet, and a connecting channel which connects the first microchannel and the second microchannel, the concentration cell has the first microchannel, a substance adapted to adsorb and desorb the gases to be analyzed, and provided in part of the first microchannel, and a heating source for heating the substance for adsorbing and desorbing the gases to be analyzed, and the detection cell has the second microchannel, an optical fiber for entry of ultraviolet light for spectrophotometric analysis into the second microchannel, and an optical fiber for exit of the ultraviolet light for spectrophotometric analysis from the second microchannel.

The above and other objects, effects, features and advantages of the present invention will become more apparent from the following description of embodiments thereof taken in conjunction with the accompanying drawings.

DETAILED DESCRIPTION OF THE PREFERRED EMBODIMENTS

Figure 1:
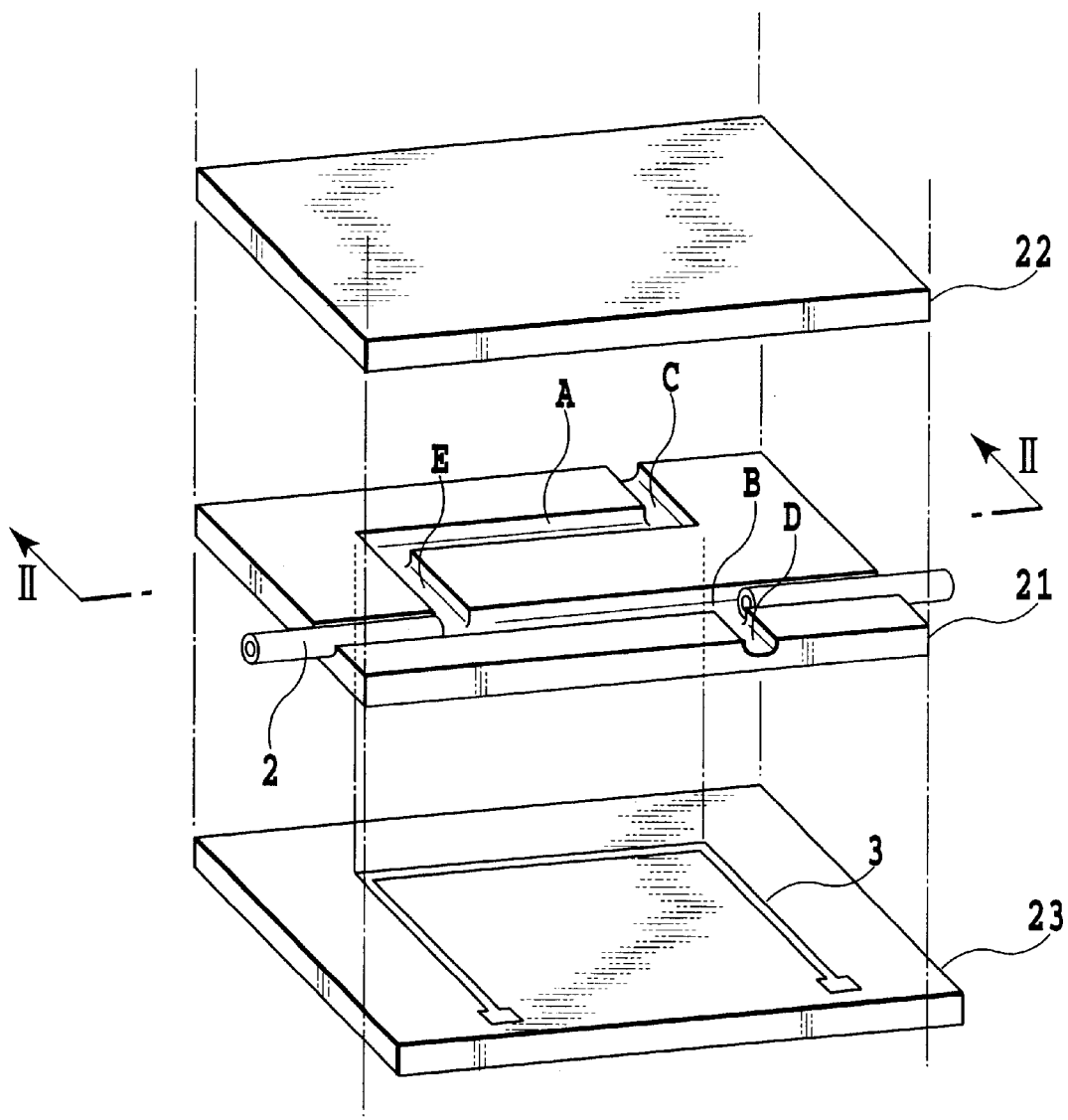
FIG. 1 is a perspective view of a micro-fluidic cell for optical detection of gases shown in Embodiment 1.

The micro-fluidic cell for optical detection of gases according to the present invention comprises a microchannel, a concentration cell, and a detection cell.

The "microchannel" comprises a first microchannel having a gas inlet included in the concentration cell, a second microchannel having a gas outlet included in the detection cell, and a connecting channel which connects the first microchannel and the second microchannel. The connecting channel is a microchannel for connecting the concentration cell and the detection cell and capable of flow analysis of trace samples.

The "concentration cell" has the first microchannel, an adsorbent-loaded portion having part of the first microchannel loaded with a substance for adsorbing and desorbing target gases (i.e., an adsorbent), and functions to heat the entire adsorbent-loaded portion. Preferably, a stopper for stopping the adsorbent is provided in a part downstream from the adsorbent-loaded portion in the concentration cell.

The "detection cell" has the second microchannel, and has a spectrophotometric function capable of measuring the ultraviolet absorption spectrum within the microchannel by optical fibers connected to both ends of the second microchannel.

The respective portions are to be downsized enough to fulfill the following conditions:

The channel of the "concentration cell" measures about several hundred micrometers in width and several centimeters in length so that the adsorbent in an amount sufficient to concentrate the samples can be loaded, the area of contact between the adsorbent and gases is large, and the temperature is uniform during heating. As the stopper, a protruding can be provided downstream from the adsorbent-loaded portion. The protruding for stopping the adsorbent has the same width as the adsorbent-loaded channel, and has 10 to tens of micrometers in depth and about 1 mm in length. The heating function (heater) is adapted to heat the entire adsorbent-loaded channel, and is imparted by attaching a metallic thin film of a size comparable to the size of the adsorbent-loaded channel to the outside of the adsorbent-loaded channel, and heating the entire adsorbent-loaded channel from one side. The outside of the heater may be covered with a heat insulator such as Teflon and heated. To ensure a low electric power consumption, the heater may be patterned e.g. in a zigzag form so as to be capable of effecting efficient temperature control of the entire adsorbent-loaded portion.

Since the cell is of a microstructure, the heat capacity of the adsorbent-loaded portion is small, so that rapid heat desorption lasting about 10 to several tens of seconds can be realized to increase the efficiency of desorption upon heating.

The channel of the "detection cell" is of the size of about hundreds of micrometers in width×several centimeters in length so that the ultraviolet absorption spectrum can be measured with the optical fibers and the sample gas concentration effect can be maintained.

The size of the micro-fluidic cell for optical detection of gases according to the present invention is 3 cm×1 cm, and its thickness corresponds to the number of the substrates stuck together.

The microchannels in the micro-fluidic cell for optical detection of gases according to the present invention may all be formed on the same substrate, or different substrates, if the microchannels are through. That is, the first microchannel, the second microchannel, and the connecting channel may be formed on the same substrate. Alternatively, the first microchannel, and the second microchannel may be formed on different substrates, and the connecting channel may be formed as a through-hole for corresponding substrate portions so that when these substrates are stacked, the first microchannel and the second microchannel communicate with each other.

As the aforementioned concentration cell, it is further preferred to use a gas trapping cell further including a cold-trap channel for cold-trapping target gases after the target gases adsorbed to the adsorbent are heat-desorbed. The gas trapping cell includes a gas inlet, an adsorbent, an adsorbent-loaded channel, an adsorbent stopper provided downstream from the adsorbent-loaded channel, the cold-trap channel, a gas outlet, and a heater having the function of heating an adsorbent-loaded portion. The gas trapping cell may, of course, be used in combination with the detection cell as the concentration cell of the micro-fluidic cell for optical detection of gases according to the present invention, but may also be used by connecting to other analyzer.

The adsorbent-loaded channel of the gas trapping cell is about several (0.1 to 9) millimeters wide×tens to hundreds of micrometers deep×several millimeters long so that the adsorbent in an amount sufficient to concentrate the target gases can be loaded, the area of contact between the adsorbent and gases is sufficiently large, and the temperature is uniform during heating. A protruding as the adsorbent stopper downstream from this channel has the same width as the adsorbent-loaded channel, and has 10 to tens of micrometers in depth and about 1 mm in length. Since the cell is of a microstructure, the gas flow rate is $1/10$ to $1/100$ of that in the conventional apparatus. Consequently, such a protruding can sufficiently stop the adsorbent.

The cold-trap channel downstream from the adsorbent stopper is a channel measuring hundreds of micrometers wide, hundreds of micrometers deep, and several millimeters long. At the outside of the cold-trap channel, no heater or heat insulator is provided, and the gases are cooled by air cooling. As stated earlier, the cell is of a microstructure, so that its heat capacity is low, the cooling efficiency improves, and a refrigerant such as liquid nitrogen is unnecessary. Because of recovery by air cooling, moreover, a reheating process is not necessary. Furthermore, provision of micro pillars in the cold-trap channel lengthens the time of dwelling of the heated gases in the cold-trap channel, and thus permits more efficient cooling. Formation of a micro trench, or formation of a metallic thin film in the surface portion of the substrate corresponding to the cold-trap channel is also preferred, because a cooling effect can be increased.

The size of the entire gas trapping cell is 3 cm×1 cm, and its thickness corresponds to the number of the substrates stuck together.

Methods for producing the above-described micro-fluidic cell for optical detection of gases and the gas trapping cell described above must meet the condition that materials used for the substrates of the cells can be microfabricated, and do not decompose or generate interfering components even when heated. For connection of the optical fibers or substrates, it is necessary to use adhesion materials or adhesion processes which are free from decomposition or generation of interfering components upon heating. The shape of the microchannels needs to be such that the microchannels can be processed to sizes enough for adsorbent loading or optical fiber connection. In the present invention, therefore, Pyrex or silicon is used for the substrates of the cells. Connection of the optical fibers also employs encapsulation with low temperature sealing glass or cycloten which does not decompose or generate interfering components even at high temperatures, in comparison with adhesives such as ultraviolet curing resins in general use.

As methods for forming the channels, there can be used a simple method using a dicing saw, dry etching, wet etching, or sand blasting. Methods for formation of the heater are, for example, metal masking, lift-off technique, plating, and ion milling.

The above-described micro-fluidic cell for optical detection of gases according to the present invention is connected to an ultraviolet light source, an ultraviolet spectrophotometer, a heater power source, and a controller to constitute an apparatus, which corresponds to the measuring means for identifying components and measuring concentrations of the gases to be analyzed.

The embodiments of the present invention will now be described in detail with reference to the accompanying drawings. The invention is not restricted only to the following embodiments.

[Embodiment 1]

Figure 2:
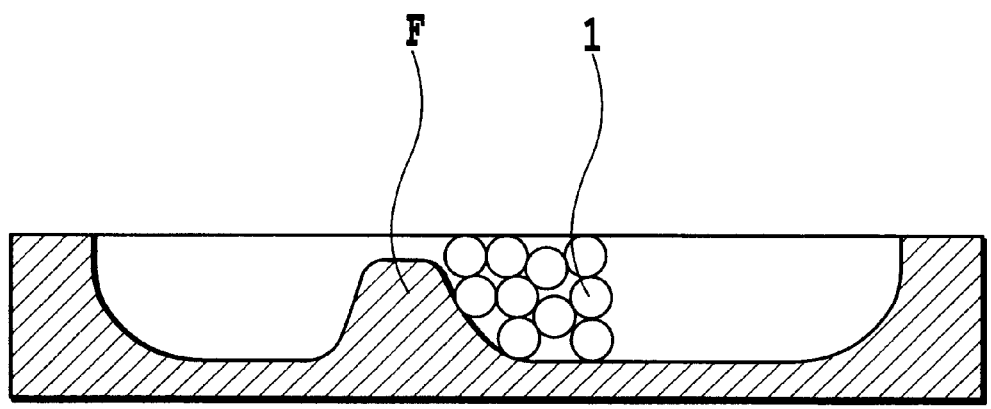
FIG. 2 is a schematic sectional view taken on line II—II of FIG. 1.

As Embodiment 1 of the present invention, a micro-fluidic cell for optical detection of gases using a Pyrex substrate and having microchannels all formed on the same substrate, and a method for producing the cell will be described based on FIGS. 1 and 2. FIG. 1 is a perspective view showing an example of a micro-fluidic cell for optical detection of gases according to the present invention. FIG. 2 is a sectional view taken on line II—II of FIG. 1.

A Pyrex substrate having a diameter of 4 inches (4×2.54 cm) and a thickness of 0.7 mm and mirror-polished on both surfaces was used. A 200 nm silicon nitride film was deposited on one surface of a Pyrex substrate by a plasma CVD system (Anelva Co.) under the conditions: nitrogen gas 140 sccm, argon-based 5% silane gas 25 sccm, pressure 20 Pa, and RF (radio frequency) electric power 40W.

On the Pyrex substrate with the silicon nitride film, patterns of trenches A to E of 0.4 mm wide and 0.4 mm deep were formed in a connected pattern, as shown in FIG. 1, with the use of a 0.4 mm thick blade by a dicing saw (Disco Co.). At the portions A to E in FIG. 1, chopper cutting method was used to form the trenches. After forming the patterns, the substrate was cut to each pattern for separating as chips to make Pyrex substrates 21. A corresponds to an adsorbent-loaded channel, B corresponds to an ultraviolet optical path/microchannel, C corresponds to a gas inlet, D corresponds to a gas outlet, and E corresponds to a connecting channel connecting the first microchannel and the second microchannel.

As shown in FIG. 2, a powder of porous glass (such as Vycor) with a pore diameter adjusted to about 4 nm was placed as an adsorbent 1 at the portion A of the trench. The trenches were formed by chopper cutting, and the trenches at both ends were shallow to form an adsorbent stopper F. Thus, upon passage of gases through the channels, the powder of porous glass moves with difficulty.

Then, a second Pyrex substrate 22 polished on both surfaces was cut to the same size as the silicon nitride film-deposited Pyrex substrate 21.

Then, the trenched substrate 21, and the flat substrate 22 without trenches were aligned within an anodic bonder (SIG-S, Union Optical Co., Ltd.). Then, anodic bonding of the silicon nitride film of the substrate 21 to the substrate 22 was performed for 10 minutes at a heater temperature of 450° C. under a voltage of −1.5 kV to bond them together. In this manner, the respective trenches A to E were used as microchannels.

Two UV multimode optical fibers 2 (core diameter 365 micrometers, cladding diameter 400 micrometers, Oz Optics, Ltd.) mirror-polished at end surfaces were prepared, and inserted into the microchannel B such that their polished surfaces face each other. Then, a slurry of a powder of low temperature sealing glass (Asahi Technoglass 7590) dissolved in an isoamyl acetate solution containing 1% of nitrocellulose was coated onto portions of the optical fibers protruding from the microchannel B. After coating the sealing glass, they were dried at 110° C. to evaporate the organic solvent. Then, the composite was heated to 350° C. to drive away the nitrocellulose, and then burned at 450° C. to seal the optical fibers 2 to the Pyrex cell. Then, the composite was slowly returned to room temperature, surplus fibers were removed with a cutter, and the four side surfaces were mirror-polished.

Then, a third Pyrex substrate 23 was introduced into a sputtering device (Seed Lab. Co.), where sputter deposition of platinum was performed at a discharge power of 500 W and at 0.005 Torr in an argon atmosphere to form a heater 3 followed by sputter deposition of titanium. At this time, a predetermined thin film pattern was obtained using a metal mask. This Pyrex substrate 23 was cut to a predetermined size by a dicing saw, and then disposed under, and in intimate contact with, the optical fiber-encapsulated cell. The heater 3 made of platinum may be disposed directly below the porous glass, and by supplying an electric current, can control the temperature of the porous glass efficiently.

A micro-fluidic cell for optical detection of gases was produced in the above-described manner.

Figure 3:
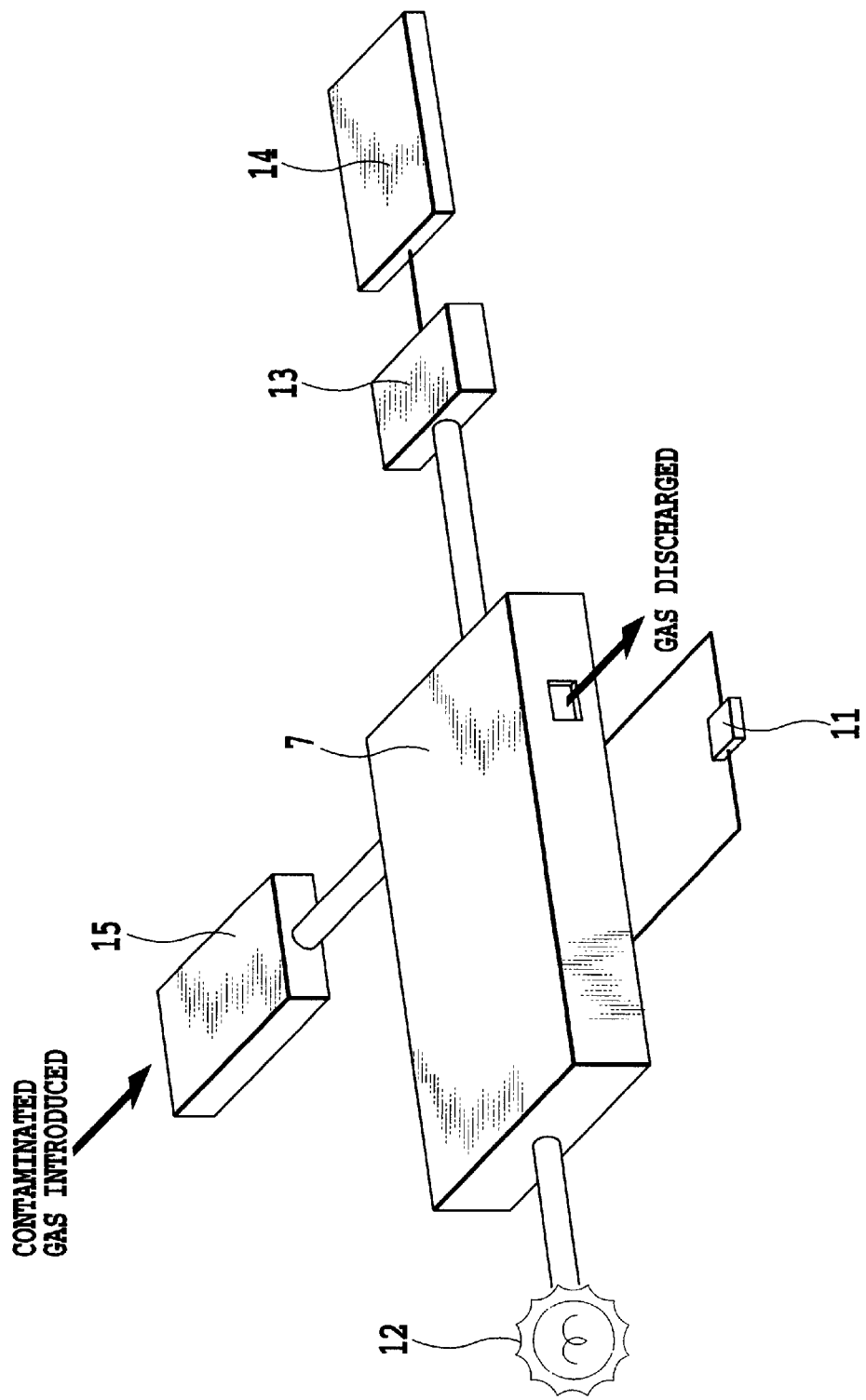
FIG. 3 is a schematic drawing showing an example of an apparatus for optical detection of gases according to the present invention.

The procedure for measurement will be described with reference to FIG. 3. FIG. 3 is a schematic drawing showing an example of an apparatus for optical detection of gases which is equipped with the micro-fluidic cell for optical detection of gases according to the present invention.

The micro-fluidic cell for optical detection of gases 7 shown in FIG. 1 was connected to a heater power source 11, an ultraviolet light source 12, an ultraviolet spectrometer 13, and a controller 14. They constitute an apparatus, which corresponds to the measuring means for identifying components and measuring concentrations of the gases to be analyzed. Air polluted by target gases was introduced by a pump 15 through the gas inlet C of the micro-fluidic cell for optical detection of gases 7 produced in the above-described manner to adsorb and fix the target gases to the adsorbent loaded in the adsorbent-loaded channel A. After a certain time of the air passage, the heater 3 was heated by current supply using the heater power source 11. By this measure, the temperature of the heater was raised to thermal-desorption temperatures for respective components of the target gases adsorbed to the adsorbent 1, thereby desorbing the respective components one after another. The desorbed, separated components of the target gases was introduced into the ultraviolet optical path/microchannel B via the connecting channel E. The target gases was detected by optical absorption spectroscopy via the optical fibers 2 connected to the ultraviolet light source 12 and the ultraviolet spectrophotometer 13. The gases after measurement was discharged through the gas outlet D.

Analysis of the gases using the micro-fluidic cell for optical detection of gases showed the sensitivity to be 5 ppm in a concentration time of 30 minutes and the accuracy to be within 20%.

[Embodiment 2]

Figure 4:
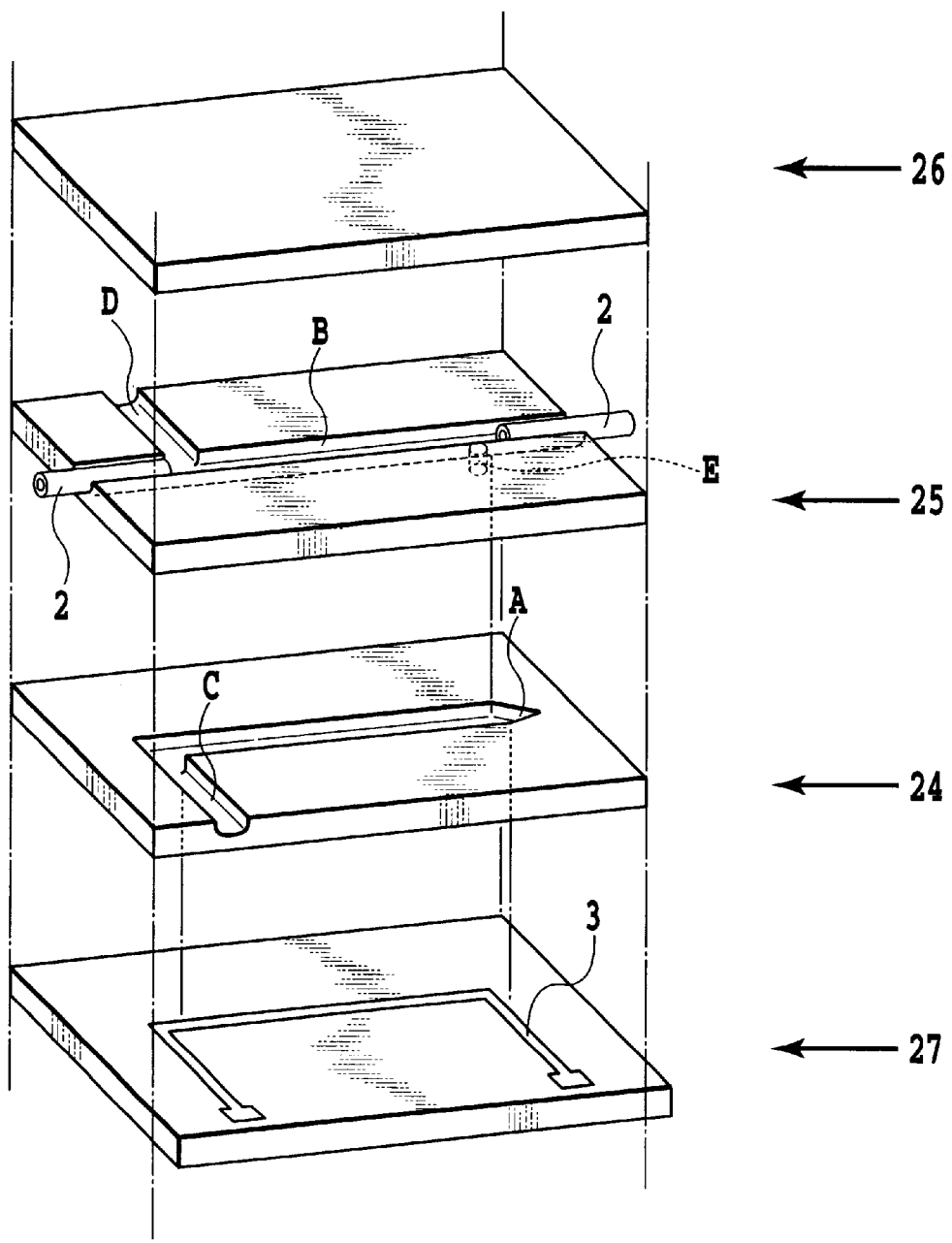
FIG. 4 is a perspective view of a micro-fluidic cell for optical detection of gases shown in Embodiment 2.

As Embodiment 2 of the present invention, a configuration of a micro-fluidic cell for optical detection of gases using a Pyrex substrate mirror-polished on both surfaces and a silicon substrate with thermally oxidized layers, mirror-polished on both surfaces, and having a first microchannel and a second microchannel formed on different substrates and connected together by a connecting channel as a through-hole, and a method for producing the cell will be described based on FIG. 4. FIG. 4 is a view showing an example of a micro-fluidic cell for optical detection of gases according to the present invention.

A Pyrex substrate having a diameter of 4 inches (4×2.54 cm) and a thickness of 0.7 mm and mirror-polished on both surfaces was used. On the Pyrex substrate, patterns of trenches A and C of 0.4 mm wide and 0.4 mm deep were formed in a shape, as shown in 24 of FIG. 4, with the use of a 0.4 mm thick blade by a dicing saw, in chopper cutting of the same manner as in Embodiment 1. A corresponds to an adsorbent-loaded channel, and C corresponds to a gas inlet. After forming the patterns, each pattern is cut for separating as chips to make Pyrex substrates 24. A powder of porous glass was placed as an adsorbent 1 at the portion A of the trench.

Then, on a silicon substrate with thermally oxidized layers having a diameter of 4 inches (4×2.54 cm) and a thickness of 0.7 mm and mirror-polished on both surfaces, patterns of trenches B and D of 0.4 mm wide and 0.4 mm deep were formed in a shape, as shown in FIG. 4, with the use of a 0.4 mm thick blade by a dicing saw. At the portions B and D in FIG. 4, chopper cutting method was used to form the trenches. B corresponds to an ultraviolet optical path/microchannel, and D corresponds to a gas outlet. Further, a hole with a diameter of 0.4 mm was formed in a portion E of FIG. 4 by means of an electroplated diamond drill. E corresponds to a connecting channel. After forming the patterns, the substrate was cut to each pattern and to the same size as the Pyrex substrate 24 for separating as chips to make silicon substrates 25.

Then, the two trenched substrates, 24 and 25, were aligned within an anodic bonder (SIG-S, Union Optical Co., Ltd.) such that the trench A and the trench B are brought into communication by the through-hole E, as shown in FIG. 4. Then, anodic bonding was performed under the conditions of Embodiment 1 to bond the substrates together. A flat Pyrex substrate 26 with no trench was further bonded to the upper layer by performing anodic bonding under the same conditions.

Then, UV multimode optical fibers 2 were inserted into the ultraviolet optical path/microchannel B of the silicon substrate with thermally oxidized layers under the same conditions as in Embodiment 1, and fixed to the cell.

Then, sputter deposition of titanium and platinum was performed for a Pyrex substrate 27 under the same conditions as in Embodiment 1 to form a heater 3 as described in FIG. 4. This Pyrex substrate 27 was cut to a predetermined size by a dicing saw, and then disposed under, and in contact with, the cell having the aforementioned optical fibers 2 sealed therein (i.e., the lower surface of the substrate 24). The heater 3 was located at the position corresponding to the adsorbent-loaded portion.

A micro-fluidic cell for optical detection of gases was produced in the above-described manner. The micro-fluidic cell for optical detection of gases was used in the apparatus for optical detection of gases as shown in FIG. 3, and measurement with the apparatus was performed in the same manner as in Embodiment 1. The measurement showed the sensitivity to be 5 ppm in a concentration time of 30 minutes and the accuracy to be within 20% such as the measurement in Embodiment 1.

[Embodiment 3]

Figure 5:
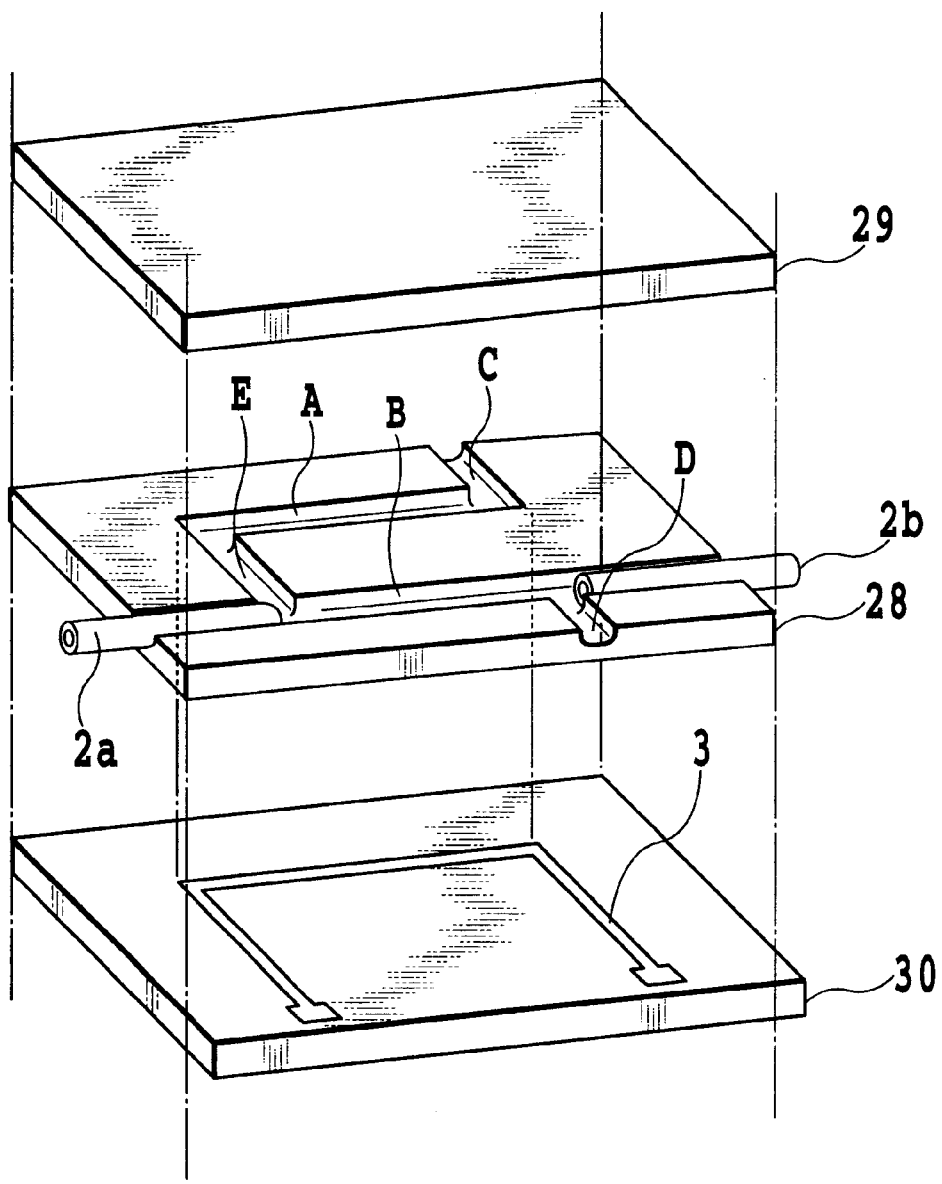
FIG. 5 is a perspective view of a micro-fluidic cell for optical detection of gases shown in Embodiment 3.

As Embodiment 3 of the present invention, a configuration of and a method for production of a micro-fluidic cell for optical detection of gases using Pyrex substrates mirror-polished on both surfaces and a silicon substrate with thermally oxidized layers mirror-polished on both surfaces, and having microchannels all formed on the same substrate will be described based on FIG. 5. FIG. 5 is a perspective view showing an example of a micro-fluidic cell for optical detection of gases according to the present invention.

A silicon substrate with thermally oxidized layers having a diameter of 4 inches (4×2.54 cm) and a thickness of 0.7 mm and mirror-polished on both surfaces was used. On the silicon substrate with thermally oxidized layers, patterns of trenches A of to E 0.4 mm wide and 0.4 mm deep were formed in a shape, as shown in FIG. 5, with the use of a 0.4 mm thick blade by a dicing saw, in the same manner as in Embodiment 1. After forming the patterns, the substrate was cut to each pattern for separating as chips to make substrates 28. A corresponds to an adsorbent-loaded channel, B corresponds to an ultraviolet optical path/microchannel, C corresponds to a gas inlet, D corresponds to a gas outlet, and E corresponds to a connecting channel. A powder of porous glass was placed as an adsorbent 1 at the portion A of the trench.

Then, a second Pyrex substrate 29 polished on both surfaces was cut to the same size as the substrate 28.

Then, the trenched substrate 28 and the untrenched substrate 29 were aligned within an anodic bonder (SIG-S, Union Optical Co., Ltd.). Then, anodic bonding was performed under the conditions of Embodiment 1 to bond the substrates together.

Then, two UV multimode optical fibers 2a, 2b were inserted into the trench B of the silicon substrate in the same manner as in Embodiment 1, and fixed to the cell. The optical fiber 2a connected to the light source was one having a tip processed in a semispherical form (available from, for example, Kyowa Densen Co.). Since such an optical fiber was used, a light flux was prevented from expanding within the cell, and the power of the light source could be used with high efficiency. The optical fiber 2b connected to the spectrometer was flat at the tip, and was able to pick up light, expanding within the cell, with high efficiency.

Then, sputter deposition of titanium and platinum was performed for a third Pyrex substrate 30 under the same conditions as in Embodiment 1 to form a heater 3. This Pyrex substrate 30 was cut to a predetermined size by a dicing saw, and then disposed under, and contact with, the cell having the aforementioned optical fibers 2a, 2b sealed therein (i.e., the lower surface of the substrate 28). The heater 3 is located at the position corresponding to the adsorbent-loaded portion A.

A micro-fluidic cell for optical detection of gases was produced in the above-described manner. The micro-fluidic cell for optical detection of gases is used, for example, in the apparatus for optical detection of gases shown in FIG. 3, and measurement with the apparatus was performed in the same manner as in Embodiment 1. The measurement showed the sensitivity to be 5 ppm in a concentration time of 30 minutes and the accuracy to be within 20% such as the measurement in Embodiment 1.

[Embodiment 4]

Figure 6:
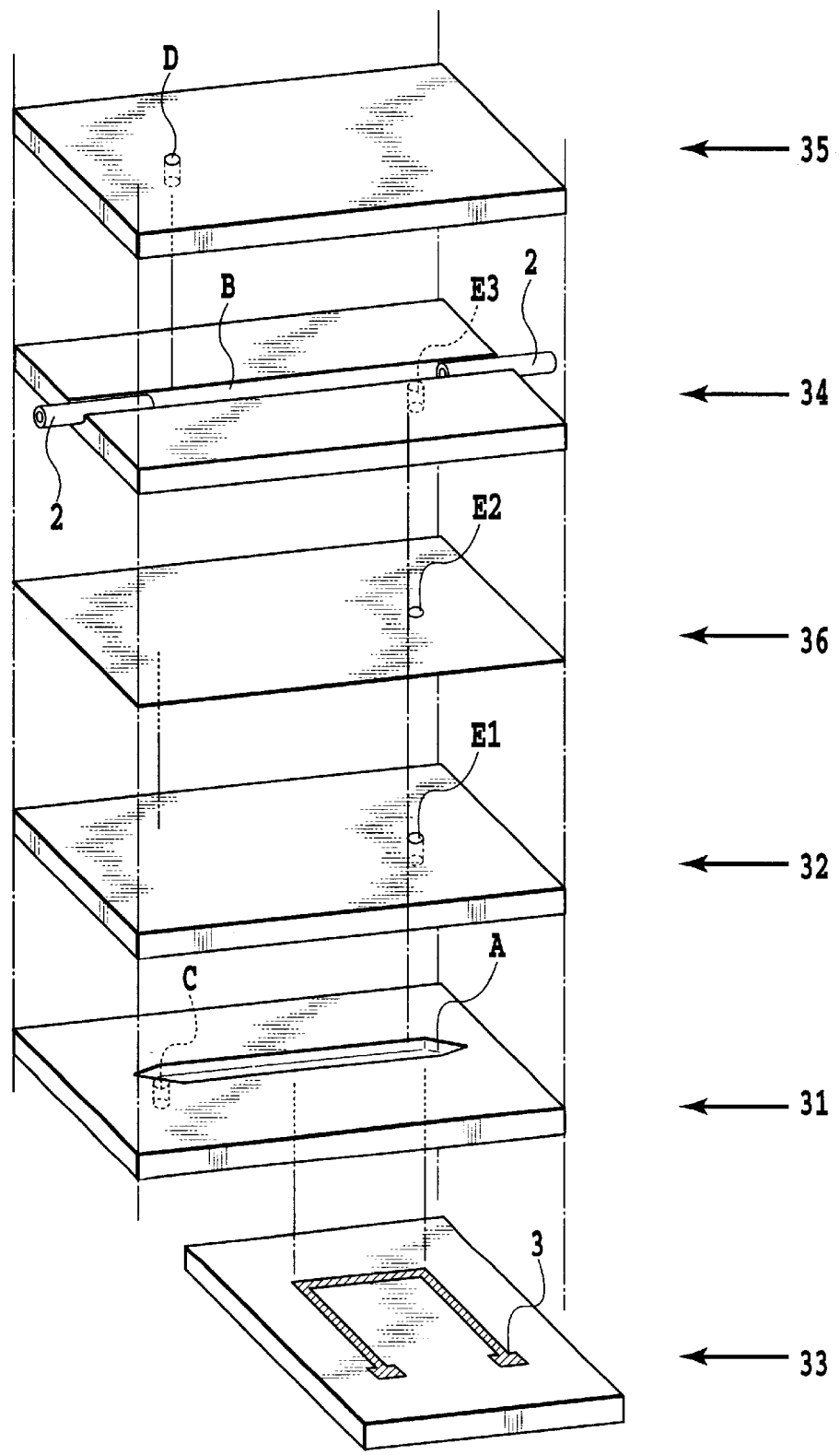
FIG. 6 is a perspective view of a micro-fluidic cell for optical detection of gases shown in Embodiment 4.

As Embodiment 4 of the present invention, a configuration of and a method for production of a micro-fluidic cell for optical detection of gases using a combination of a concentration cell and a detection cell constituted in different substrates will be described based on FIG. 6. FIG. 6 is a perspective view showing an example of a micro-fluidic cell for optical detection of gases according to the present invention.

First, the configuration and method for production of a concentration cell for gases will be described using FIG. 6.

A Pyrex substrate having a diameter of 4 inches (4×2.54 cm) and a thickness of 0.7 mm, mirror-polished on both surfaces, and provided with a silicon nitride film was used. On the Pyrex substrate, patterns of trench A of 0.4 mm wide and 0.4 mm deep were formed in a shape, as shown in FIG. 6, with the use of a 0.4 mm thick blade by a dicing saw, in the chopper cutting of the same manner as in Embodiment 1. After forming the patterns, the substrate was cut to each pattern for separating as chips to make Pyrex substrates 31. A corresponds to an adsorbent-loaded channel. A powder of porous glass was placed as an adsorbent 1 at the trench portion A. Further, a hole with a diameter of 0.4 mm was formed in a portion C of FIG. 6 by means of an electroplated diamond drill. C corresponds to a gas inlet.

Then, a Pyrex substrate 32 polished on both surfaces was cut to the same size as the substrate 31, and a hole with a diameter of 0.4 mm was formed in the portion E1 of FIG. 6 by means of an electroplated diamond drill. E1 corresponds to part of a connecting channel.

Then, the trenched substrate 31 and the untrenched substrate 32 were aligned within an anodic bonder (SIG-S, Union Optical Co., Ltd.), as shown in FIG. 6, and anodic bonding was performed under the conditions of Embodiment 1 to bond the substrates together. The through-hole E1 was located so as to communicate with the trench A.

Then, sputter deposition of titanium and platinum was performed for a Pyrex substrate 33 under the same conditions as in Embodiment 1 to form a heater 3 as described in FIG. 6. This substrate 33 was cut to a predetermined size by a dicing saw. The substrate 33 was disposed contact with the lower surface of the aforementioned substrate 31 to produce a concentration cell for gases. The heater 3 was located at the position corresponding to the adsorbent-loaded portion A.

Next, the configuration and method for production of a detection cell will be described using FIG. 6.

A Pyrex substrate having a diameter of 4 inches (4×2.54 cm) and a thickness of 0.7 mm, mirror-polished on both surfaces, and provided with a silicon nitride film was used. On the Pyrex substrate, patterns of a trench B of 0.4 mm wide and 0.4 mm deep was formed in a shape, as shown in FIG. 6, with the use of a 0.4 mm thick blade by a dicing saw. Further, a hole with a diameter of 0.4 mm was formed in a portion E3 in each trench B of FIG. 4 by means of an electroplated diamond drill. B corresponds to an ultraviolet optical path/microchannel, and E3 corresponds to part of the connecting channel. The Pyrex substrate was cut to each pattern and to the same size as the substrate 31 for separating as chips to make Pyrex substrates 34. Then, a Pyrex substrate 35 polished on both surfaces was cut to the same size as the substrate 34, and a hole with a diameter of 0.4 mm was formed in a portion D of FIG. 6 by means of an electroplated diamond drill. D corresponds to a gas outlet.

Then, the trenched substrate 34 and the untrenched substrate 35 were aligned within an anodic bonder (SIG-S, Union Optical Co., Ltd.), as shown in FIG. 6, and anodic bonding was performed under the conditions of Embodiment 1 to bond the substrates together. The through-hole D was located so as to communicate with the trench B.

Then, UV multimode optical fibers 2 were inserted into the trench B of the substrate 34 in the same manner as in Embodiment 1, and set in place to form a detection cell.

Then, a seal packing formed by cutting a fluorocarbon resin film to the same size as the substrate 32 was used as a film 36, and a hole with a diameter of 0.4 mm was formed in a portion E2 of FIG. 6. The film 36 was sandwiched between the concentration cell and the detection cell as shown in FIG. 6, and pressed from both sides, whereby the film 36 acts as a gasket. The through-holes E1, E2 and E3 were in alignment and constitute a single through-hole, thus corresponding to a connecting channel. The trenches A and B communicate by this connecting channel, and the trench A was open at the through-hole C, while the trench B was open at the through-hole D.

A micro-fluidic cell for optical detection of gases was produced in the above-described manner. The resulting micro-fluidic cell for optical detection of gases was used, for example, in the apparatus for optical detection of gases shown in FIG. 3, and measurement with the apparatus was performed in the same manner as in Embodiment 1. The measurement showed the sensitivity to be 5 ppm in a concentration time of 30 minutes and the accuracy to be within 20% such as the measurement in Embodiment 1.

[Embodiment 5]

Figure 7:
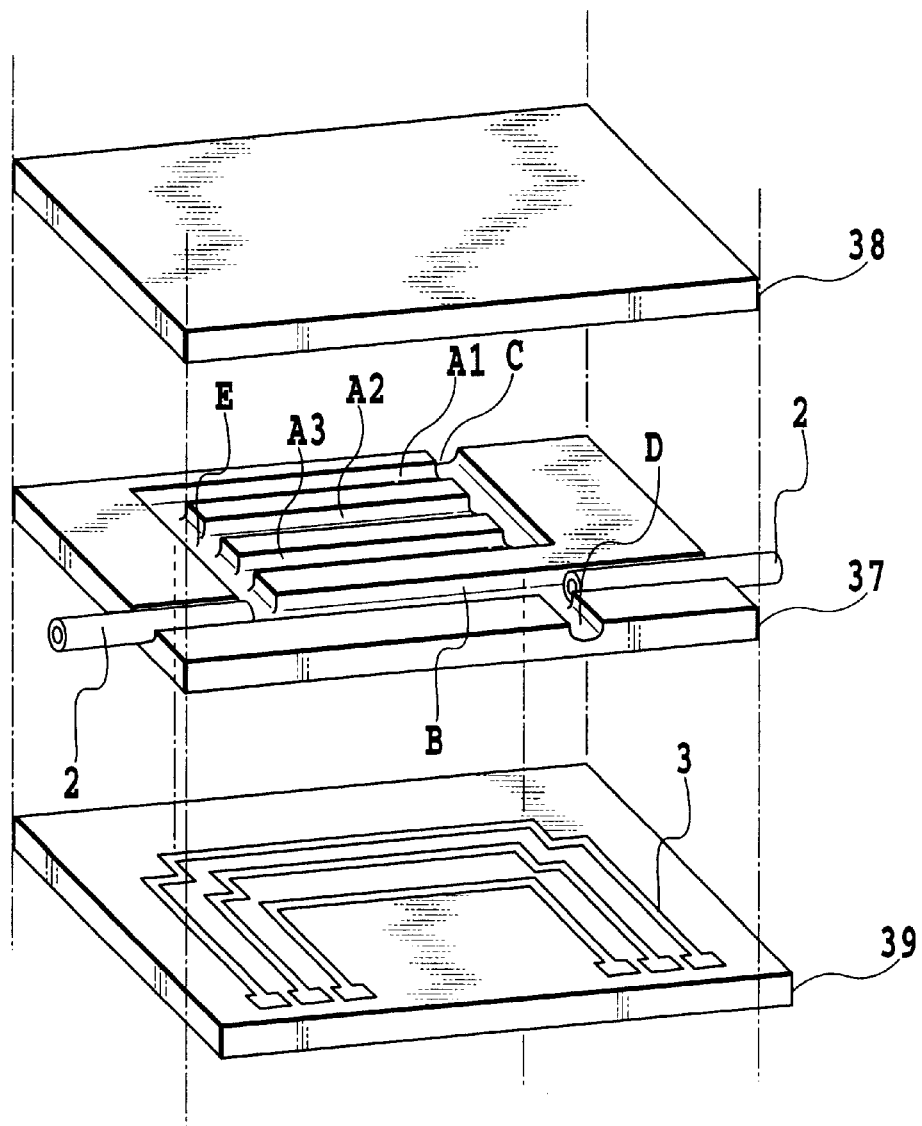
FIG. 7 is a perspective view of a micro-fluidic cell for optical detection of gases shown in Embodiment 5.

As Embodiment 5 of the present invention, the configuration and method for production of a micro-fluidic cell for optical detection of gases, in which three types of porous glass have been loaded, will be described based on FIG. 7. FIG. 7 is a perspective view showing an example of a micro-fluidic cell for optical detection of gases according to the present invention.

A nitride film was formed in the same manner as in Embodiment 1 on a Pyrex substrate having a diameter of 4 inches (4×2.54 cm) and a thickness of 0.7 mm and mirror-polished on both surfaces. On the Pyrex substrate, patterns of trenches A to E of 0.4 mm wide and 0.4 mm deep were formed in a shape, using chopper cutting as shown in FIG. 7, with the use of a 0.4 mm thick blade by a dicing saw. A1 to A3 correspond to adsorbent-loaded channels, B corresponds to an ultraviolet optical path/microchannel, C corresponds to a gas inlet, D corresponds to a gas outlet, and E corresponds to a connecting channel. Then, The Pyrex substrate was cut to each pattern for separating as chips to make Pyrex substrates 37. Powders of porous glass with pore diameters adjusted to 1 nm, 4 nm and 10 nm, respectively, were placed as an adsorbent 1 at the portions A1 to A3 of the trenches. These porous glass materials having the different pore diameters have different adsorptivities.

Then, a second Pyrex substrate 38 polished on both surfaces was cut to the same size as the substrate 37.

Then, the trenched substrate 37 and the untrenched substrate 38 were aligned within an anodic bonder (SIG-S, Union Optical Co., Ltd.), and anodic bonding was performed under the conditions of Embodiment 1 to bond the substrates together.

Then, two UV multimode optical fibers 2 were inserted into the trench B of the Pyrex substrate 37 under the same conditions as in Embodiment 1, and fixed to the cell.

Then, sputter deposition of titanium and platinum was performed for a third Pyrex substrate 39 under the same conditions as in Embodiment 1 to form a heater portion 3 as shown in FIG. 7. This Pyrex substrate 39 was cut to a predetermined size by a dicing saw, and then disposed under, and contact with, the cell having the aforementioned optical fibers sealed therein (i.e., the lower surface of the substrate 37). The resulting three platinum patterns may be disposed directly below the porous glass in the trenches A1 to A3, and upon supply of an electric current, can control the temperature of the porous glass efficiently and independently. These patterns can be changed to match the gas desorption properties of the porous glass.

A micro-fluidic cell for optical detection of gases was produced in the above-described manner. The so obtained micro-fluidic cell for optical detection of gases was used, for example, in the apparatus for optical detection of gases shown in FIG. 3, and measurement with the apparatus was performed in the same manner as in Embodiment 1. The measurement showed the sensitivity to be 5 ppm in a concentration time of 30 minutes and the accuracy to be within 20% such as the measurement in Embodiment 1. Also the measurement showed three type of gases could detect separately.

[Embodiment 6]

Figure 8:
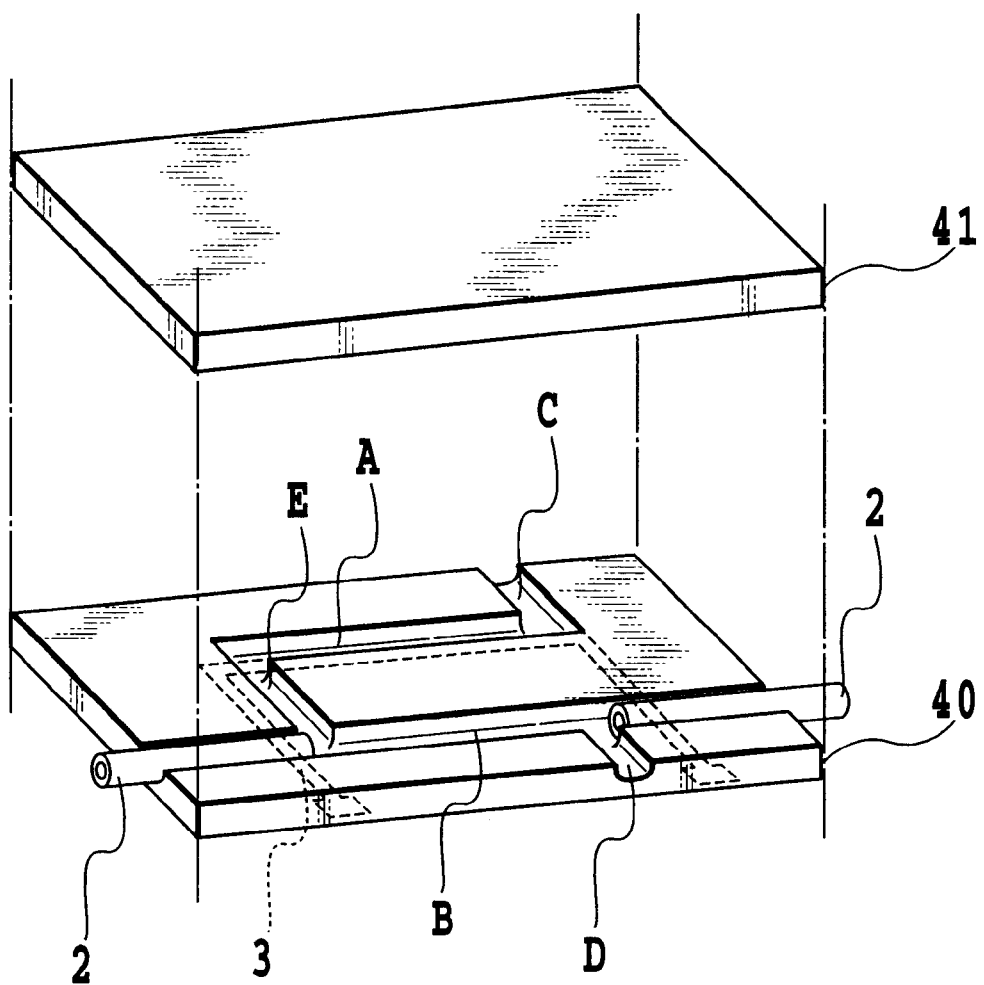
FIG. 8 is a perspective view of a micro-fluidic cell for optical detection of gases shown in Embodiment 6.

As Embodiment 6 of the present invention, a configuration of and a method for production of a micro-fluidic cell for optical detection of gases using a Pyrex substrate mirror-polished on both surfaces and a silicon substrate with thermally oxidized layers mirror-polished on both surfaces, and having microchannels all formed on the same substrate will be described based on FIG. 8. FIG. 8 is a perspective view showing an example of a micro-fluidic cell for optical detection of gases according to the present invention.

Sputter deposition of titanium and platinum was performed on the back surface of a silicon substrate with thermally oxidized layers having a diameter of 4 inches (4×2.54 cm) and a thickness of 0.7 mm and mirror-polished on both surfaces. The sputter deposition was carried out in a patter as shown in FIG. 8 under the same conditions as in Embodiment 1 to form heater portions 3. Then, in the surface opposite to the heater-formed surface, patterns of trenches A to E of 0.4 mm wide and 0.4 mm deep were formed in a shape, as shown in FIG. 8, with the use of a 0.4 mm thick blade by a dicing saw. Then, the substrate was cut to each pattern for separating as chips to make Pyrex substrates 40. A corresponds to an adsorbent-loaded channel, B corresponds to an ultraviolet optical path/microchannel, C corresponds to a gas inlet, D corresponds to a gas outlet, and E corresponds to a connecting channel. A powder of porous glass was placed as an adsorbent 1 at the portion A of the trench.

Then, a second Pyrex substrate 41 polished on both surfaces was cut to the same size as the substrate 40.

Then, the trenched substrate 40 and the untrenched flat substrate 41 were aligned within an anodic bonder (SIG-S, Union Optical Co., Ltd.). Then, anodic bonding was performed under the conditions of Embodiment 1 to bond the substrates together.

Then, two UV multimode optical fibers 2 were inserted into the trench B of the silicon substrate 40 in the same manner as in Embodiment 1, and fixed to the cell.

A micro-fluidic cell for optical detection of gases was produced in the above-described manner.

The resulting micro-fluidic cell for optical detection of gases was used, for example, in the apparatus for optical detection of gases shown in FIG. 3, and measurement with the apparatus was performed in the same manner as in Embodiment 1. The measurement showed the sensitivity to be 5 ppm in a concentration time of 30 minutes and the accuracy to be within 20% such as the measurement in Embodiment 1. However, the response was fast as compared with Embodiment 1, since the heater 3 was in closer portion by the adsorbent.

Embodiments 1 to 6 are embodiments using the micro-fluidic cell for optical detection of gases which had no cold-trap channel in the concentration cell for gases. In the present invention, as stated earlier, it is more preferred to use a gas trapping cell having a cold-trap channel as the concentration cell. Herein below, embodiments using the gas trapping cell will be described.

[Embodiment 7]

Figure 9:
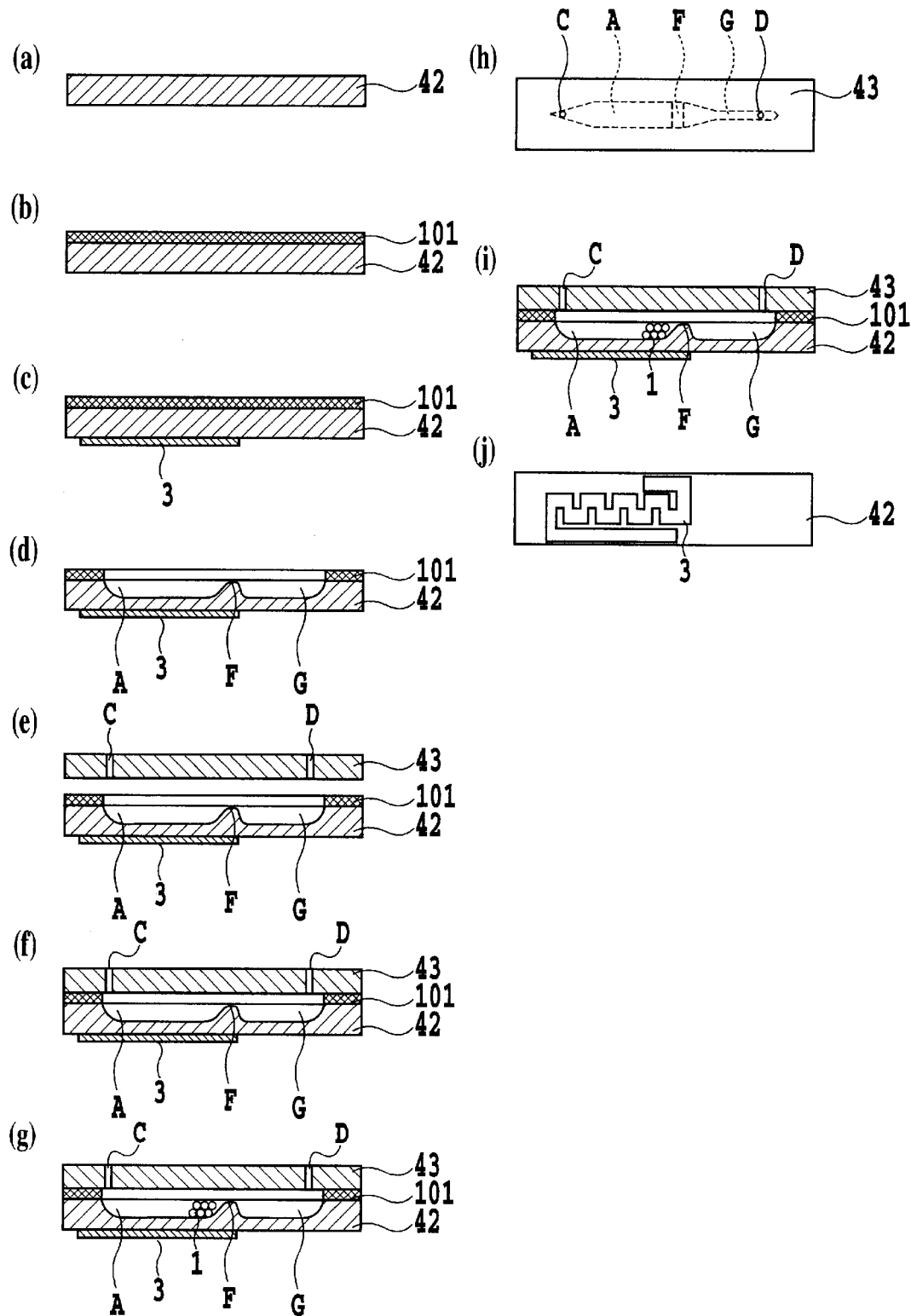
FIGS. 9(a) to 9(g) are views illustrating a method for producing a gas trapping cell shown in Embodiment 7.
FIG. 9(h) is a plan view of a gas trapping cell shown in Embodiment 7.
FIG. 9(i) is a sectional view.
FIG. 9(j) is a rear view.

As Embodiment 7 of the present invention, a configuration of, and a method for production of, a gas trapping cell using a Pyrex substrate will be described based on FIGS. 9(*a*) to 9(*j*). FIGS. 9(*a*) to 9(*j*) are views showing an example of the method for producing the gas trapping cell according to the present invention.

A Pyrex substrate 42 having a diameter of 4 inches (4×2.54 cm) and a thickness of 0.5 mm and mirror-polished on both surfaces, as shown in FIG. 9(*a*), was used. A 200 nm silicon nitride film 101 was deposited on one surface of the Pyrex substrate 42, as shown in FIG. 9(*b*), by a plasma CVD system (Anelva Co.) under the conditions: nitrogen gas 140 sccm, argon-based 5% silane gas 25 sccm, pressure 20 Pa, and RF (radio frequency) electric power 40W. For an explanation, FIGS. 9(a) to 9(d) illustrate not whole substrate 42, but part of only one gas trapping cell.

The Pyrex substrate 42 with the silicon nitride film 101 was introduced into a sputtering device (Seed Lab. Co.), where titanium and platinum were sputter deposited in this order on the surface, on which the silicon nitride film 101 had not been deposited, at a discharge power of 500 W and at 0.005 Torr in an argon atmosphere, as shown in FIG. 9(c). At this time, a platinum/titanium thin film patterns 3 having a predetermined heater shape were obtained using a metal mask. The thin film heater 3 may be disposed directly below the adsorbent-loaded portion A, and upon supply of an electric current, can control the temperature efficiently.

Then, on the substrate 42 with the silicon nitride film 101, trenches of about 16 mm long, 0.2 mm deep, and 2.4 mm wide, and having a stepped structure F 0.03 mm deep in a midway portion were formed as shown in FIG. 9(d), with the use of a 0.2 mm thick blade by a dicing saw (Disco Co.) to form an adsorbent-loaded channel A. A trench of about 8 mm long, about 0.8 mm wide, and 0.2 mm deep was also formed in the same manner to form a cold-trap channel G. The width 2.4 mm of the adsorbent-loaded channel A in FIG. 9 was formed by carving 12 trenches with a width of 0.2 mm. Trench formation was performed in the chopper cutting mode, with a height direction of the blade being controlled, to form the adsorbent stopper step F midway in the trench. Similarly, the width 0.8 mm of the cold-trap channel G in the drawing consisted of 4 trenches with a width of 0.2 mm. After forming trenches, the substrate 42 was cut to each pattern for separating to make the structure of FIG. 9(d).

Then, as shown in FIG. 9(e), holes with a diameter of 0.5 mm were formed in portions corresponding to a gas inlet C and a gas outlet D in the drawing in a second Pyrex substrate 43 polished on both surfaces with the use of an electroplated diamond drill. The substrate 43 was cut to the same size as the Pyrex substrate 42.

Then, the trenched substrate 42, and the untrenched substrate 43 were aligned within an anodic bonder (SIG-S, Union Optical Co., Ltd.) so that the gas inlet C and the adsorbent-loaded channel A would communicate and the gas outlet D and the cold-trap channel G would communicate, as shown in FIG. 9(f). Then, anodic bonding of the silicon nitride film 101 of the substrate 42 to the substrate 43 was performed for 10 minutes at a heater temperature of 500° C. under a voltage of −1.2 kV to bond them together. Then, as shown in FIG. 9(g), an adsorbent 1 was introduced into the adsorbent-loaded channel A through the hole of the gas inlet C.

In the above-described manner, there was produced a gas trapping cell in which the adsorbent-loaded channel A, the adsorbent 1 as an adsorber and desorber of target gases, the thin film heater 3 as a heating source, and the cold-trap channel G for target gases have been integrated on an integral assembly of the substrate 42 and the substrate 43, as shown in FIGS. 9(h), 9(i) and 9(j).

FIG. 9(h) is a plan view of the gas trapping cell produced in the manner of the present embodiment, FIG. 9(i) is a sectional view, and FIG. 9(j) is a rear view.

Next, the effects ascribed to the cell production method and structure will be described. Formation of the adsorbent-loaded channel A, cold-trap channel G, and adsorbent stopper step F was performed using the cutting method by a dicing saw. Trench formation by a dicing saw can form only a linear trench, and is greatly restricted by the pattern of the trench, but can obtain a deep trench easily and in a short time as compared with etching method. The trench depth can be changed in a single trench by controlling the position of the blade in its height direction. In the present embodiment, the height of the blade in the trench was controlled, whereby the adsorbent stopper step F could be formed to prevent run-off of the adsorbent 1. The adsorbent-loaded channel A as a wide trench having many linear channels arranged parallel could increase the amount of the adsorbent 1 loaded, while keeping the resistance during gas passage low. The cold-trap channel G with a few trenches arranged parallel had a sectional area which is ⅓ of that of the adsorbent-loaded channel A. Thus, the gases desorbed from the adsorbent-loaded channel A were efficiently concentrated in the cold-trap channel G. The thin film heater 3 was not patterned on the lower surface of the cold-trap channel G, so that the gases desorbed from the adsorbent-loaded channel A were efficiently cooled during passage through the cold-trap channel G.

An example of the procedure for measurement will be described. The air polluted by target gases was introduced through the gas inlet C of FIG. 9 to adsorb and fix the target gases to the adsorbent 1 loaded in the adsorbent-loaded channel A. After a certain time of air passage, air passage was stopped, and the heater 3 was heated by current supply. By this measure, the temperature of the heater was raised to thermal-desorption temperatures for respective components of the target gases adsorbed to the adsorbent 1, thereby desorbing the respective components one after another. The desorbed, separated components of the target gases were recovered by air cooling at the cold-trap channel G. After thorough recovery, air passage was started again, and introduced into the detection cell as described in any of Embodiments 1 to 6 of the detector via the gas outlet D.

Figure 10:
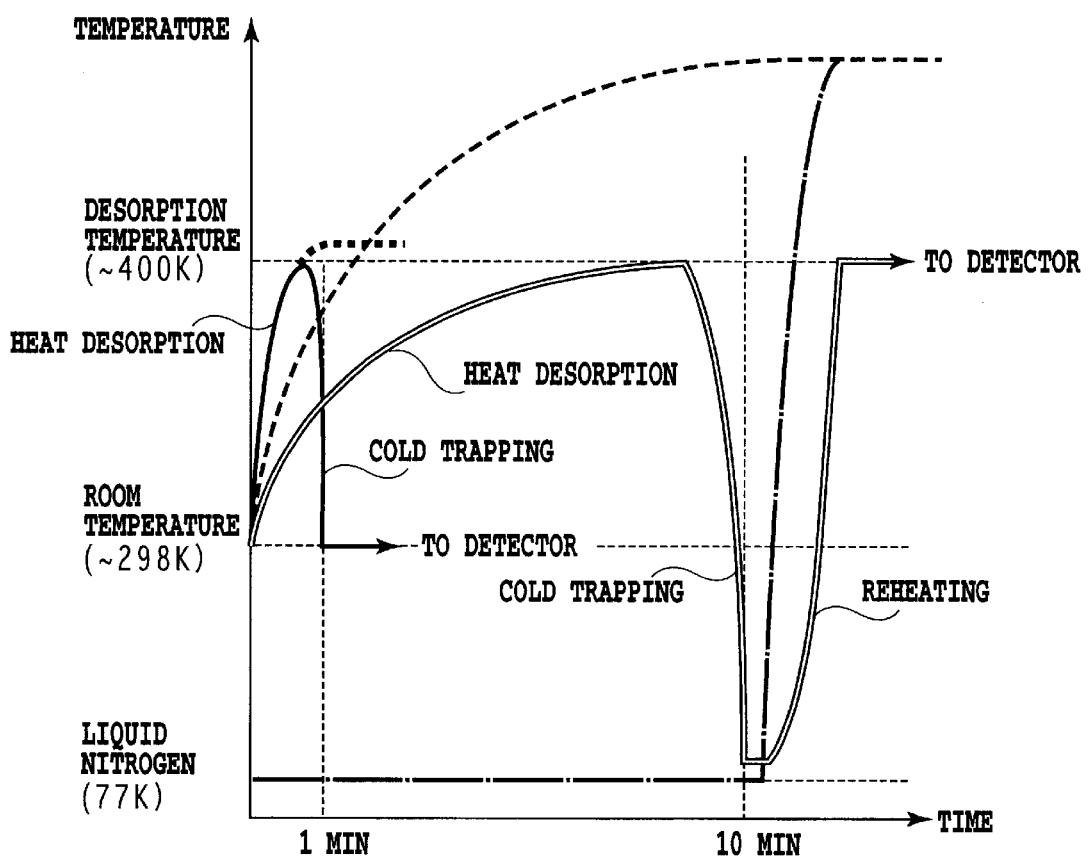
FIG. 10 is a graph comparing the thermal characteristics of the apparatus and target gases during operation of the gas trapping cell shown in Embodiment 7 and the prior art.

If the target gas is composed of a single component, the thermal characteristics of the apparatus and target gas in Embodiment 7 of the present invention and in the prior art will be described with reference to FIG. 10. According to the prior art, as stated earlier, at a site for which analysis should be made, the air containing a target gas was introduced into a collection tube, and the target gas was collected into the adsorbent. Then, the collection tube was heated to desorb the target gas adsorbed to the adsorbent as a concentrated gas. The concentrated gas was recovered again into a cold-trap device where liquid nitrogen was circulated. Then, the trapped gas was reheated at a stretch, and introduced into a gas chromatographic analyzer. As noted from this, the desorption process in the prior art had to set the temperature of the heater at a considerably higher value than the desorption temperature of the gas, and required a time of about 10 minutes. According to Embodiment 7 of the present invention, by contrast, the temperature of the heater may be set to be slightly higher than the desorption temperature, and the process was completed in a short time of about 1 minute. The subsequent cold-trap process, according to the prior art, involves cooling the gas to the temperature of liquid nitrogen, and reheating the solidified gas to a temperature close to the desorption temperature, and introducing it into the detector. According to the embodiment 7 of the present invention, the gas was cold-trapped at room temperature, and could be introduced as such into the detector.

Figure 11:
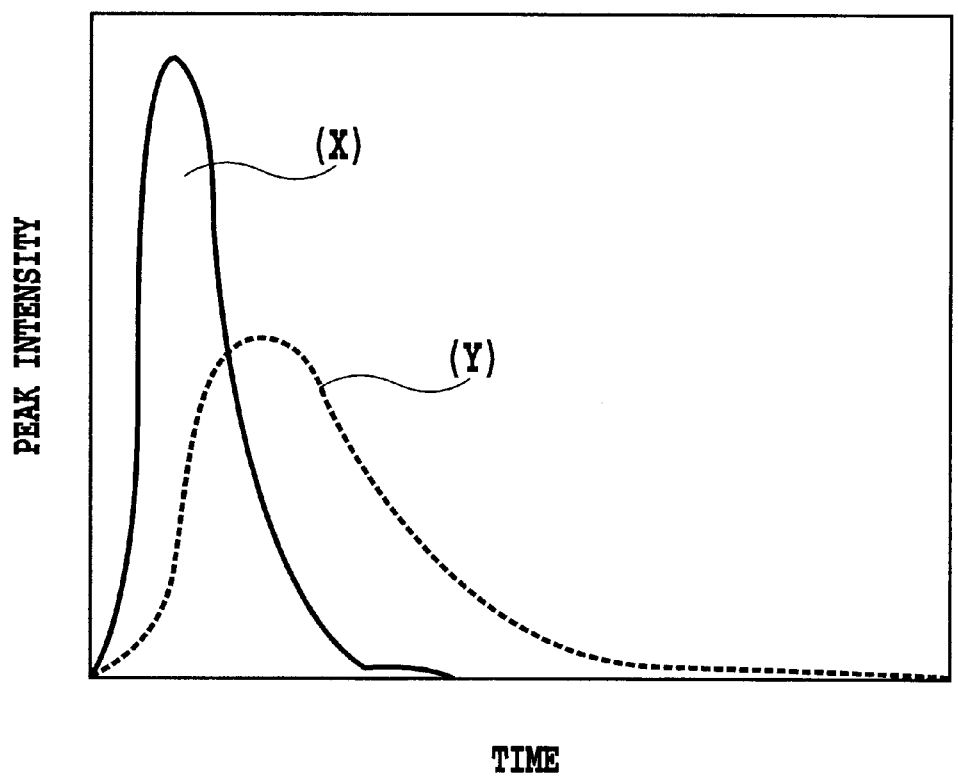
FIG. 11 is a graph comparing the gas detection peak characteristics obtained with the use of the gas trapping cell shown in Embodiment 7 and the concentration cell shown in Embodiment 1.

FIG. 11 compares the flow characteristics of detection gases shown when the gas trapping cell of Embodiment 7 was used (X) and when the micro-fluidic cell for optical detection of gases of Embodiment 1 was used (Y). When the micro-fluidic cell for optical detection of gases of Embodiment 1 (Y) was used, the target gases adsorbed and concentrated in the microchannel loaded with the adsorbent were introduced sequentially into the detection channel upon thermal desorption. At this time, the target gases tend to diffuse in the optical path/microchannel of the detection cell, and their peak width tends to increase. With the gas trapping cell (X) obtained from Embodiment 7, the thermal desorbed gases were cold-trapped again, whereby diffusion of the target gases in the optical path/microchannel of the detection cell was prevented, thus narrowing the peak width. Consequently, the peak value for measurement of the same amount of sample heightens. Provision of the cold-trap channel is thus found to be effective in increasing detection sensitivity and to be more preferred.

[Embodiment 8]

Figure 12:
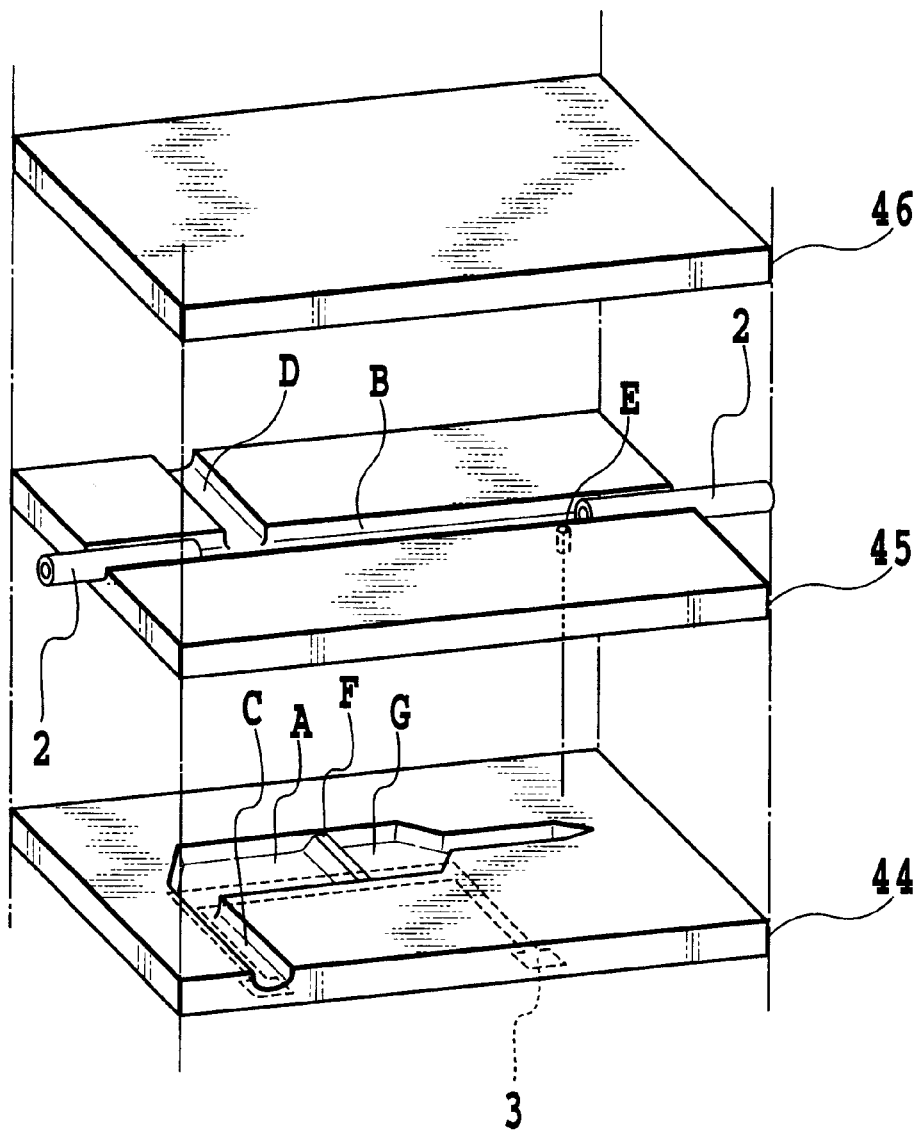
FIG. 12 is a perspective view of a micro-fluidic cell for optical detection of gases shown in Embodiment 8.

As Embodiment 8 of the present invention, a configuration of, and a method for production of, a micro-fluidic cell for optical detection of gases using a Pyrex substrate and provided with a cold-trap channel will be described based on FIG. 12. FIG. 12 is a view showing an example of the structure of and the method for production of the micro-fluidic cell for optical detection of gases according to the present invention.

A Pyrex substrate having a diameter of 4 inches (4×2.54 cm) and a thickness of 0.5 mm and mirror-polished on both surfaces was used. A 200 nm silicon nitride film was deposited on one surface of the Pyrex substrate by a plasma CVD system (Anelva Co.) under the conditions: nitrogen gas 140 sccm, argon-based 5% silane gas 25 sccm, pressure 20 Pa, and RF (radio frequency) electric power 40W. The Pyrex substrate with the silicon nitride film was introduced into a sputtering device (Seed Lab. Co.), where titanium and platinum were sputter deposited in this order on the surface opposite to the silicon nitride film-deposited surface at a discharge power of 500 W and at 0.005 Torr in an argon atmosphere. At this time, a thin film heater 3 having a predetermined heater shape and comprising a platinum/titanium thin film pattern was obtained using a metal mask. The heater 3 may be disposed directly below the adsorbent-loaded portion A, and upon supply of an electric current, can control the temperature efficiently.

Then, in the portion of the substrate with the silicon nitride film surface, a trench of about 16 mm long, 0.2 mm deep, and 2.4 mm wide, having an adsorbent stopper step F of 0.03 mm deep in a midway portion was formed in an elongated shape, as shown in FIG. 12, with the use of a 0.2 mm thick blade by a dicing saw (Disco Co.) to form an adsorbent-loaded channel A. A trench of about 8 mm long, about 0.8 mm wide, and 0.2 mm deep was also formed in the same manner to form a cold-trap channel G. The width 2.4 mm of the adsorbent-loaded channel A in FIG. 12 was formed by carving 12 trenches with a width of 0.2 mm. Trench formation was performed in the chopper cutting mode, with a height direction of the blade being controlled, to form an adsorbent stopper step F midway in the trench. Similarly, the width 0.8 mm of the cold-trap channel G in the drawing consists of 4 trenches with a width of 0.2 mm. C connected to the adsorbent-loaded channel A denotes a gas inlet. After forming the patterns, the substrate was cut to each pattern for separating as chips to make substrates 44.

Then, in a Pyrex substrate having a diameter of 4 inches and a thickness of 0.7 mm, mirror-polished on both surfaces, and provided with a silicon nitride film, trenches B and D of 0.4 mm wide and 0.4 mm deep were formed in a shape, as shown in FIG. 12, with the use of a 0.4 mm thick blade by a dicing saw. Further, a hole with a diameter of 0.4 mm was formed in a portion E in each trench B of FIG. 12 by means of an electroplated diamond drill. B corresponds to an ultraviolet optical path/microchannel, D corresponds to a gas outlet, and E corresponds to a connecting channel. After forming the patterns, the substrate was cut to each pattern and the same size as the substrate 44 for separating as chips to make substrates 45.

Then, the two trenched substrates 44 and 45 were aligned within an anodic bonder (SIG-S, Union Optical Co., Ltd.), as shown in FIG. 12. Then, anodic bonding was performed for 10 minutes at a heater temperature of 500° C. under a voltage of −1.2 kV to bond the substrates together. Further, an untrenched flat Pyrex substrate 46 was bonded onto the substrate 45 by performing anodic bonding under the same conditions. Then, an adsorbent 1 was introduced through the microchannel C to load the adsorbent 1 into the adsorbent-loaded channel A.

Two UV multimode optical fibers 2 (core diameter 365 micrometers, cladding diameter 400 micrometers, Oz Optics, Ltd.) mirror-polished at end surfaces were prepared, and inserted into the microchannel B such that their polished surfaces faced each other. Then, a slurry of a powder of low temperature sealing glass (Asahi Technoglass 7590) dissolved in an isoamyl acetate solution containing 1% of nitrocellulose was coated onto portions of the optical fibers protruding from the microchannel B. After coating, they were dried at 110° C. to evaporate the organic solvent. Then, the cell was heated to 350° C. to drive away the nitrocellulose, and then burned at 450° C. to seal the optical fibers to the Pyrex cell. Then, the cell was slowly returned to room temperature, surplus fibers were removed with a cutter, and the four side surfaces were mirror-polished.

In the above-described manner, a micro-fluidic cell for optical detection of gases was produced.

The resulting micro-fluidic cell for optical detection of gases was used, for example, in the apparatus for optical detection of gases shown in FIG. 3, and measurement was made in accordance with the following procedure: Air containing target gases was introduced through the gas inlet C of FIG. 12 to adsorb and fix the target gases to the adsorbent 1 loaded in the adsorbent-loaded channel A. After a certain time of air passage, air passage was stopped, and the heater 3 was heated by current supply. By this measure, the temperature of the heater was raised to thermal-desorption temperatures for respective components of the target gases adsorbed to the adsorbent 1, thereby desorbing the respective components one after another. The desorbed, separated components of the target gases were recovered by air cooling at the cold-trap channel G. After thorough recovery, air passage was started again, and detection of the contaminating substances by optical absorption spectroscopy was carried out via the optical fibers 2 connected to the ultraviolet light source 12 and the ultraviolet spectrophotometer 13. The gases after measurement were discharged through the gas outlet D. In the case that the measurement was performed under the same condition as the Embodiment 1, the results of the present embodiment showed one order larger peak height and narrow peak width as compared with Embodiment 1. Then, the micro-fluidic cell for optical detection of gases in the present embodiment has the sensitivity of 0.5 ppm in a concentration time of 30 minutes and the accuracy within 20%.

[Embodiment 9]

As Embodiment 9 of the present invention, a configuration of, and a method for production of, a gas trapping cell using a Pyrex substrate will be described based on FIGS. 13(a) to 13(k). FIGS. 13(a) to 13(k) are views showing the method for producing the gas trapping cell according to the present invention.

Figure 13:
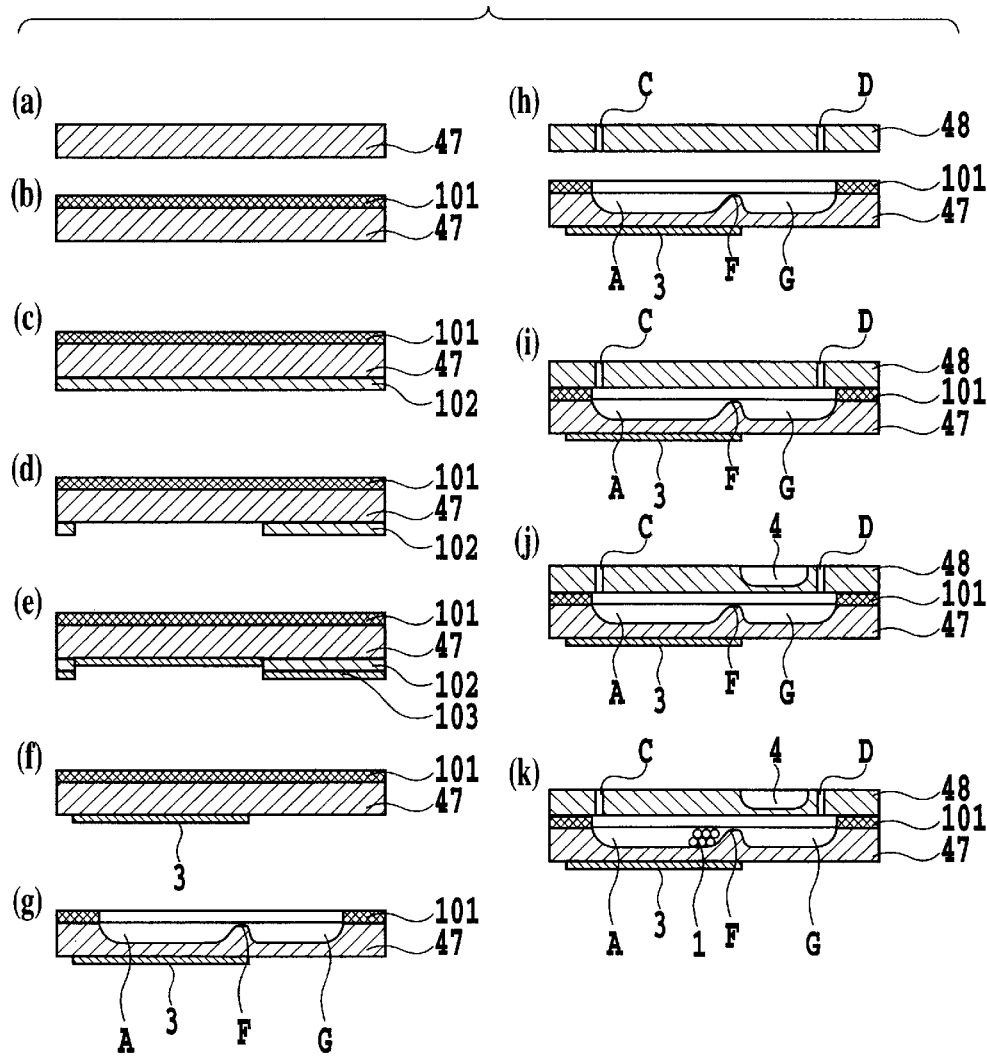
FIGS. 13(a) to 13(k) are views illustrating a method for producing a gas trapping cell shown in Embodiment 9.

As shown in FIG. 13(b), a 200 nm silicon nitride film 101 was deposited on one surface of a Pyrex substrate 47 having a diameter of 4 inches (4×2.54 cm) and a thickness of 0.5 mm, as shown in FIG. 13(a), in the same manner as in Embodiment 7. For an explanation, FIGS. 13(a) to 13(g) illustrate not whole substrate 47, but part of only one gas trapping cell.

Then, as shown in FIG. 13(c), a resist TSMR-V3 (Tokyo Ohka Kogyo Co., Ltd.) 102 was coated by a spin coater to a thickness of 1 μm onto the surface on which the silicon nitride film had not been deposited. Then, the resist coating was exposed through a heater electrode pattern with the use of an aligner PLA-501FA (CANON INC.), as shown in FIG. 13(d). The exposed layer was developed with a developer NMD-W (Tokyo Ohka Kogyo Co., Ltd.) for 40 seconds, and rinsed with running water for 60 seconds to perform patterning of the resist 102. Then, titanium and platinum were sputter deposited in this order on the resist surface of the substrate, in the same manner as in Embodiment 7, to form a platinum-titanium thin film 103, as shown in FIG. 13(e). Then, the resist on substrate 47 was removed by the lift-off technique in methyl ethyl ketone with the use of an ultrasonic cleaner to obtain certain thin film heaters 3 from the platinum/titanium pattern, as shown in FIG. 13(f).

Then, an adsorbent-loaded channel A, a cold-trap channel G, and an adsorbent stopper step F comprising trenches were formed with the silicon nitride film 101 by a dicing saw in the same manner as in Embodiment 7, as shown in FIG. 13(g). After forming trenches, the substrate 47 was cut to each pattern for separating to make the structure of FIG. 13(g).

Further, a Pyrex substrate 48 having a gas inlet C and a gas outlet D comprising holes was bonded to the substrate 47, as shown in FIGS. 13(h) and 13(i). Then, ten micro trenches 4 having a depth of 200 μm were formed at intervals of 80 μm in the Pyrex substrate 48 along the cold-trap channel G by a 40 μm thick blade, as shown in FIG. 13(j). Then, an adsorbent 1 was introduced through the gas inlet C, and loaded into the adsorbent-loaded channel A, as shown in FIG. 13(k).

In the above-described manner, a gas trapping cell was prepared.

This gas trapping cell can be combined with a detection cell to produce a micro-fluidic cell for optical detection of gases, in the same manner as in Embodiment 8. At this time, the gas inlet C is not formed in the substrate 48, but is formed in the substrate 47 so as to continue to the adsorbent-loaded channel.

In the present Embodiment 9, the lift-off method was used for formation of the thin film heater 3. According to this method, compared with the metal mask method, the fade-out of the edge portion is minimal, and the thin film heater 3 can be formed at the correct position. Furthermore, the micro trenches 4 comprising many thin trenches are formed in the surface above the cold-trap channel G to impart a large surface area. Thus, heat exchange with the outside air takes place efficiently. As a result, the cooling effect was so high that the gas trapping cell is effective for high sensitivity detection.

[Embodiment 10]

Figure 14:
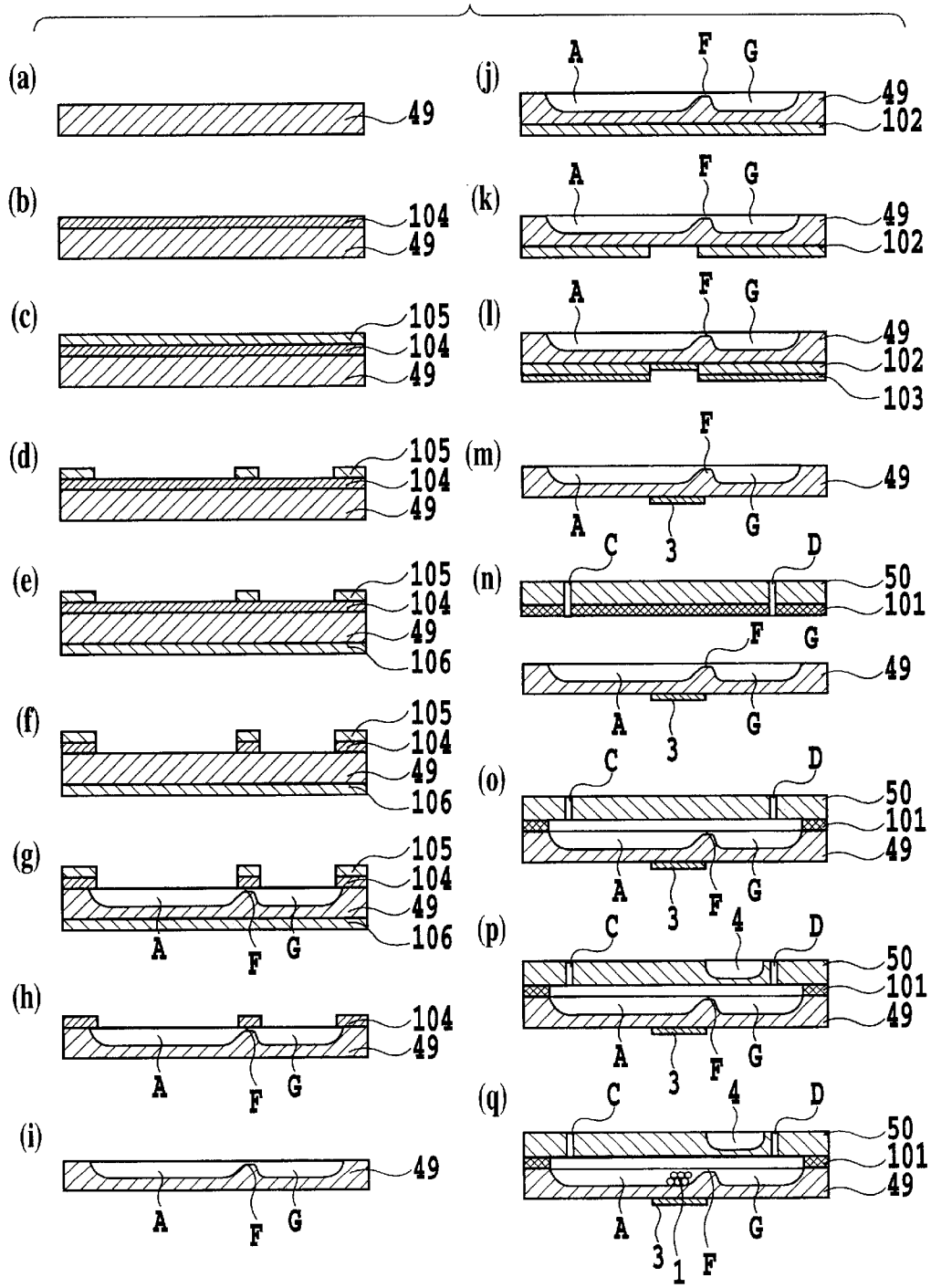
FIGS. 14(a) to 14(q) are views illustrating a method for producing a gas trapping cell shown in Embodiment 10.

As Embodiment 10 of the present invention, a configuration of, and a method for production of, a gas trapping cell using a Pyrex substrate will be described based on FIGS. 14(a) to 14(q). FIGS. 14(a) to 14(q) are views showing an example of the method for producing the gas trapping cell according to the present invention.

As shown in FIG. 14(b), chromium was sputter deposited to a thickness of 200 nm on one surface of a Pyrex substrate 49 having a diameter of 4 inches (4×2.54 cm) and a thickness of 0.5 mm, as shown in FIG. 14(a), to form a chromium film 104. For an explanation, FIGS. 14(a) to 14(m) illustrate not whole substrate 49, but part of only one gas trapping cell.

Then, as shown in FIG. 14(c), a negative photosensitive polyimide solution (Photoneece, TORAY INDUSTRIES, INC.) 105 was spin coated on the surface of the chromium film 104. After prebaking, the coating was exposed through a channel pattern with the use of an aligner PLA-501FA (CANON INC.), as shown in FIG. 14(d). The exposed layer was ultrasonically developed in a developer DV-140, and ultrasonically rinsed in isopropanol to obtain a channel pattern. After baking at 180° C., Photoneece 106 was spin coated on the surface opposite to the surface, on which the channel pattern had been formed, as shown in FIG. 14(e). Then, a predetermined baking step was completed. Then, the chromium film was etched with a chrome etching solution (Kanto Kagaku Co.), as shown in FIG. 14(f). Then, the Pyrex substrate 49 was etched to a depth of 20 μm with buffered hydrofluoric acid through the Photoneece/chromium as a mask to form an adsorbent-loaded channel A, a cold-trap channel G, and an adsorbent stopper step F comprising trenches, as shown in FIG. 14(g). Then, the Photoneece on both surfaces was peeled off by etching with oxygen RIE, as shown in FIG. 14(h). The chromium was also stripped with a chrome etchant, as shown in FIG. 14(i).

Then, thin film heaters 3 comprising a platinum/titanium thin film pattern were formed on the back surface of the Pyrex substrate 49 in the same manner as in Embodiment 9, as shown in FIGS. 14(j) to 14(m). After forming trenches, the substrate 49 was cut to each pattern for separating to make the structure of FIG. 14(m).

A 200 nm silicon nitride film 101 was deposited on one surface of a second Pyrex substrate 50 in the same manner as in Embodiment 7. An electroplated diamond drill was used to form a gas inlet C and a gas outlet D comprising holes of 0.5 mm in diameter for the purpose of gas passage. The substrate 50 was cut to the same size as substrate 49.

Then, as shown in FIG. 14(o), the substrate 50 was placed in alignment on the substrate 49, and anodic bonding was performed under the same conditions as in Embodiment 1. Then, as shown in FIG. 14(p), many micro trenches 4 were formed by a dicing saw at a position of the substrate 50 corresponding to the cold-trap channel G.

Then, an adsorbent 1 was introduced through the gas inlet C, as shown in FIG. 14(q).

In the above-described manner, a gas trapping cell was prepared. This gas trapping cell can be combined with a detection cell to produce a micro-fluidic cell for optical detection of gases, in the same manner as in Embodiment 8. At this time, the gas inlet C is not formed in the substrate 50, but is formed in the substrate 49 so as to continue to the adsorbent-loaded channel.

In the present embodiment, trench formation for the adsorbent-loaded channel A and the cold-trap channel G was performed to a depth of 20 μm by wet etching with buffered hydrofluoric acid. Since wet etching is isotropic, side etching of about 30 μm occurs. By partially disposing the Photoneece/chromium mask pattern, the adsorbent stopper step F can be formed by utilization of side etching at the relevant site. Wet etching with buffered hydrofluoric acid poses difficulty in increasing the depth of the trenches, and etching of about 20 μm is realistic. Thus, the widths of the adsorbent-loaded channel A and the cold-trap channel G were widen to lower the pressure during gas passage. Furthermore, the microchannels are shallow, and the adsorbent 1 is disposed thinly in the broad adsorbent-loaded channel A. Thus, the efficiency of heat exchange with the thin film heater 3 increases remarkably. For the same reasons, the efficiency of heat exchange at the micro trench portion 4 also increases. Thus, the concentration effect is so high that the gas trapping cell is effective for high sensitivity detection.

[Embodiment 11]

As Embodiment 11 of the present invention, a configuration of, and a method for production of, a gas trapping cell using a Pyrex substrate will be described based on FIGS. 15(a) to 15(p). FIGS. 15(a) to 15(p) are views showing an example of the method for producing the gas trapping cell according to the present invention.

As shown in FIG. 15(b), a resist TSMR-V3 (Tokyo Ohka Kogyo Co., Ltd.) 107 was coated by a spin coater to a thickness of 1 $\mu$m onto one surface of a Pyrex substrate 51 having a diameter of 4 inches (4×2.54 cm) and a thickness of 0.5 mm, as shown in FIG. 15(a). For an explanation, FIGS. 15(a) to 15(k) illustrate not whole substrate 51, but part of only one gas trapping cell.

Then, as shown in FIG. 15(c), the resist coating was exposed through a channel pattern with the use of an aligner PLA-501FA (CANON INC.). The exposed layer was developed with a developer NMD-W (Tokyo Ohka Kogyo Co., Ltd.) for 40 seconds, and rinsed with running water for 60 seconds to perform patterning of the resist. Then, chromium was sputter deposited on the substrate 51 to form a chromium film 108, as shown in FIG. 15(d). Then, the substrate 51 was subjected to the lift-off technique in methyl ethyl ketone with the use of an ultrasonic cleaner to obtain a channel pattern of chromium, as shown in FIG. 15(e). Then, the Pyrex substrate 51 was etched with $C_4F_8$ gas by a high density plasma etching device to form an adsorbent-loaded channel A and a cold-trap channel G comprising trenches 50 $\mu$m deep, as shown in FIG. 15(f). Then, the chromium was etched with a chrome etchant, as shown in FIG. 15(g).

Then, thin film heaters 3 comprising a platinum/titanium thin film pattern were formed on the back surface of the Pyrex substrate 51 in the same manner as in Embodiment 9, as shown in FIGS. 15(h) to 15(k). After forming trenches, the substrate 51 was cut to each pattern for separating to make the structure of FIG. 15(k).

Figure 15:
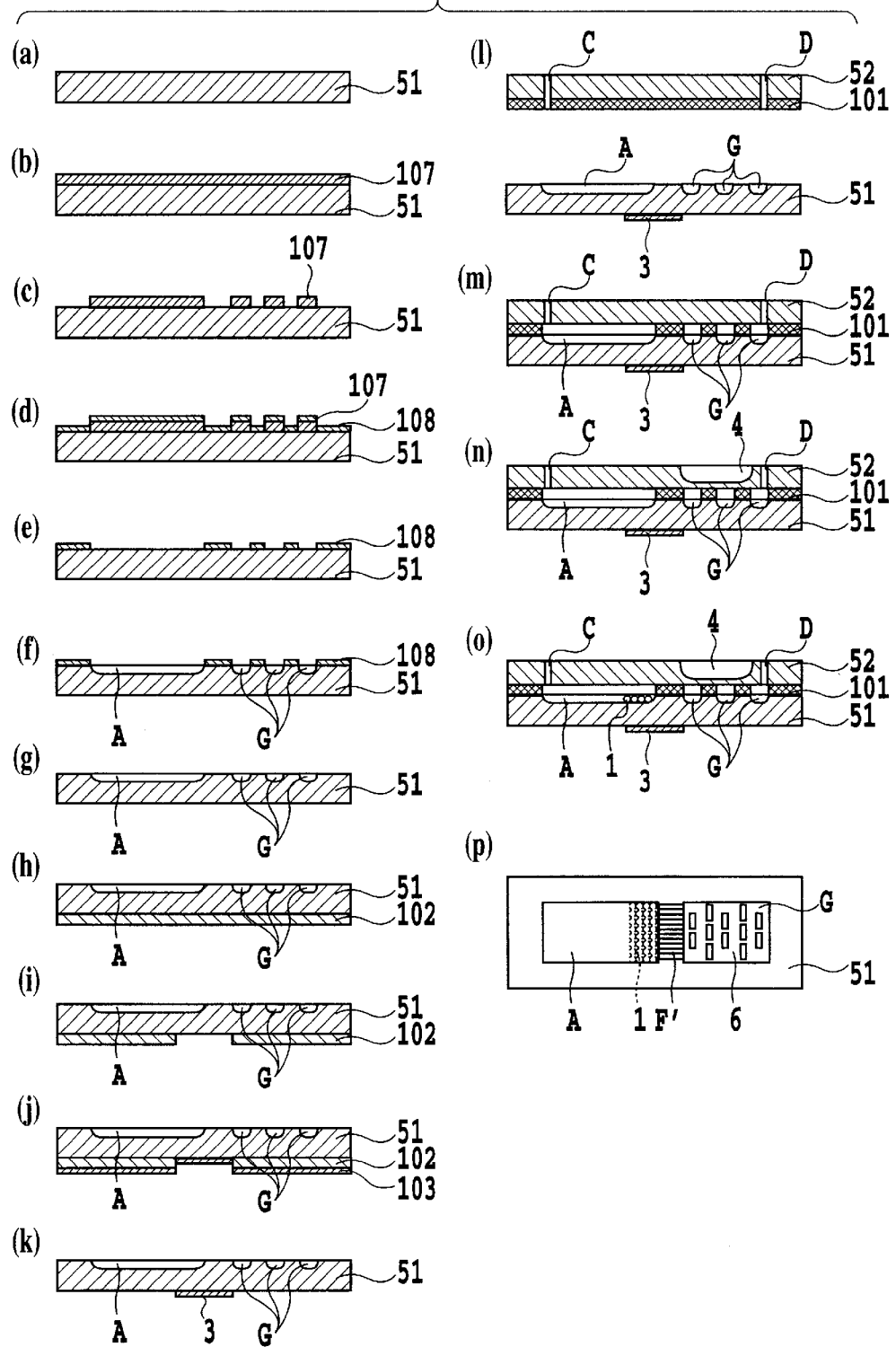
FIGS. 15(a) to 15(o) are views illustrating a method for producing a gas trapping cell shown in Embodiment 11.
FIG. 15(p) is a plan view of substrate 51 comprising in a gas trapping cell shown in Embodiment 11.

Then, a 200 nm silicon nitride film 101 was deposited on one surface of a second Pyrex substrate 52 in the same manner as in Embodiment 7, as shown in FIG. 15(1). An electroplated diamond drill was used to form a gas inlet C and a gas outlet D comprising holes of 0.5 mm in diameter for the purpose of gas passage. The substrate 52 was cut to the same size as substrate 51.

Then, as shown in FIG. 15(m), the substrate 52 was placed in alignment on the substrate 51, and anodic bonding was performed under the same conditions as in Embodiment 7. Further, as shown in FIG. 15(n), many micro trenches 4 were formed by a dicing saw at a position of the substrate 52 corresponding to the cold-trap channel G. Then, an adsorbent 1 was introduced through the gas inlet C, and loaded into the adsorbent-loaded channel A, as shown in FIG. 15(o).

In the above-described manner, a gas trapping cell was prepared. FIG. 15(p) is a plan view of the substrate 51.

The gas trapping cell prepared in the above manner can be combined with a detection cell to produce a micro-fluidic cell for optical detection of gases, in the same manner as in Embodiment 8. At this time, the gas inlet C is not formed in the substrate 52, but is formed in the substrate 51 so as to continue to the adsorbent-loaded channel.

In the present Embodiment 11, dry etching was used for formation for the adsorbent-loaded channel A and the cold-trap channel G comprising trenches. Since dry etching is anisotropic etching, side etching is minimal, and 50 $\mu$m trenches can be formed, with the shape of the mask pattern being retained. Thus, complicated and fine channel shapes can be formed easily. In the present Embodiment 11, a step structure was not used for preventing the adsorbent 1 moving, but a filter structure F' of the adsorbent was formed by photolithographic patterning. Also, many micro pillars 6 are formed in the cold-trap channel G, thus making it possible to lengthen the dwelling time in the cold-trap channel G and perform cooling efficiently. Hence, the gas trapping cell is effective for high sensitivity detection.

Furthermore, the metal mask method can be used for formation of the thin film heater in the above-described method for production of the gas trapping cell.

In the above-described method for production of the gas trapping cell, moreover, methods using a dicing saw can be used for formation of trenches for the adsorbent-loaded channel and the cold-trap channel having the adsorbent stopper step.

[Embodiment 12]

As Embodiment 12 of the present invention, a configuration of, and a method for production of, a gas trapping cell using a Pyrex substrate will be described based on FIGS. 16(a) to 16(j). FIGS. 16(a) to 16(j) are views showing an example of the method for producing the gas trapping cell according to the present invention.

A 200 nm silicon nitride film 101 was deposited on one surface of a Pyrex substrate 42 in the same manner as in Embodiment 7. For an explanation, FIGS. 16(a) to 16(d) illustrate not whole substrate 42, but part of only one gas trapping cell.

Figure 16:
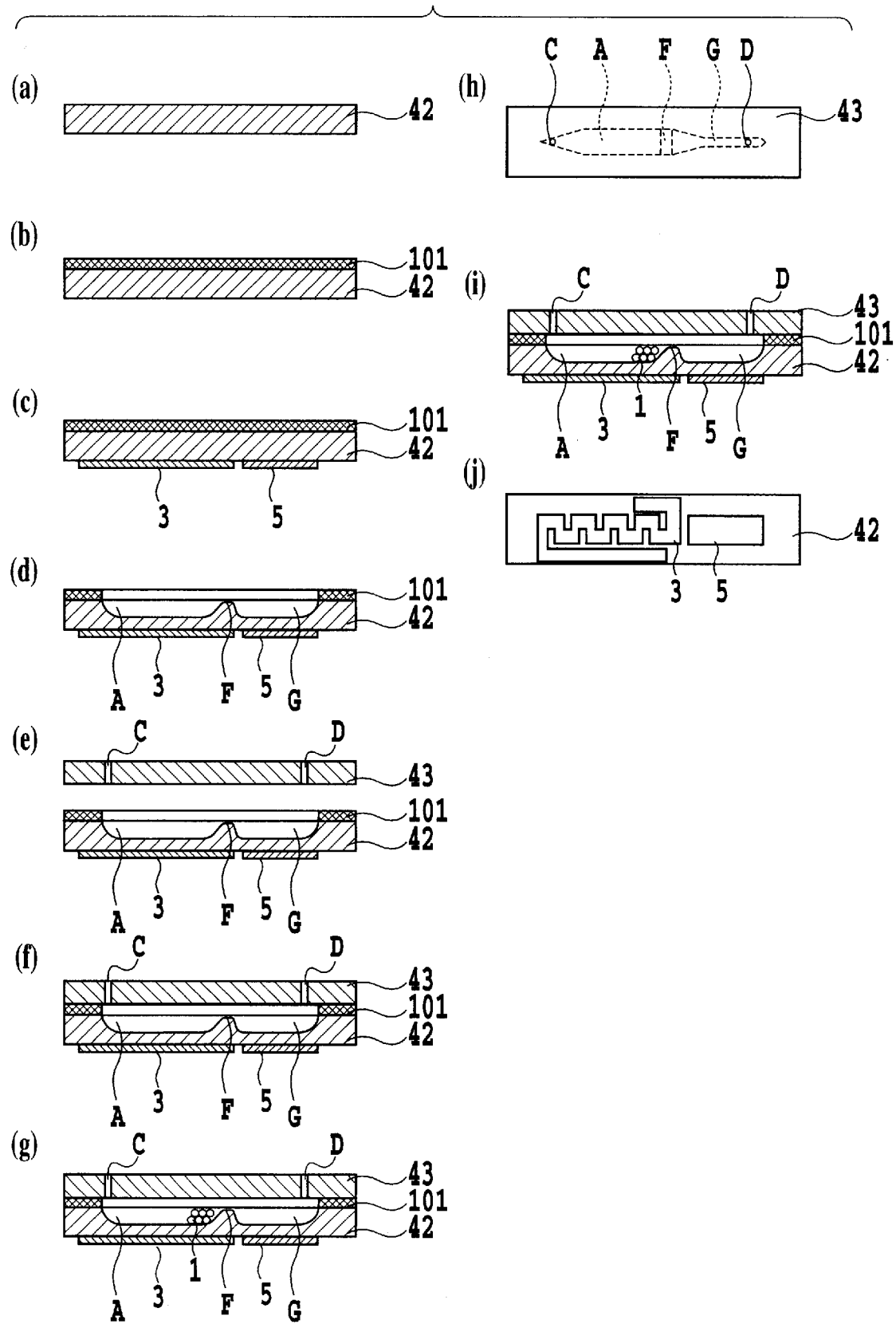
FIGS. 16(a) to 16(g) are views illustrating a method for producing a gas trapping cell shown in Embodiment 12.
FIG. 16(h) is a plan view of a gas trapping cell shown in Embodiment 12.
FIG. 16(i) is a sectional view.
FIG. 16(j) is a rear view.

The Pyrex substrate 42 with the silicon nitride film 101 was introduced into a sputtering device (Seed Lab. Co.), where titanium and platinum were sputter deposited in this order on the surface, on which the silicon nitride film 101 had not been deposited, at a discharge power of 500 W and at 0.005 Torr in an argon atmosphere, as shown in FIG. 16(c). At this time, a thin film heater 3 having a predetermined heater shape and comprising a platinum/titanium thin film pattern and a cooling metal having a predetermined cooling metal shape were obtained using a metal mask.

Subsequently, the same procedure as in Embodiment 7 was performed to prepare a gas trapping cell as shown in FIGS. 16(d) to 16(g).

FIG. 16(h) is a plan view of the gas trapping cell produced in the manner of the present embodiment, FIG. 16(i) is a sectional view, and FIG. 16(j) is rear view.

Next, the structure of the cell and the effects attributed to the structure will be mentioned. The gas trapping cell obtained in the present embodiment was the same as in Embodiment 7, except that the thin film heater 3 is not patterned, but the cooling metal was provided, on the bottom surface of the substrate at the position corresponding to the cold-trap channel G. As the neighboring heater portion increases in temperature, the temperature of the cold-trap channel also slightly rises. However, because of the cooling metal, the heat dissipation efficiency at the cold-trap channel increases, and the cooling effect due to air cooling becomes high. Thus, gases desorbed at the adsorbent-loaded channel A are efficiently cooled during passage through the cold-trap channel G.

In the above-described manner, the gas trapping cell was prepared. This gas trapping cell can be combined with a detection cell to produce a micro-fluidic cell for optical detection of gases, in the same manner as in Embodiment 8. At this time, the gas inlet C is not formed in the substrate 43, but is formed in the substrate 42 so as to continue to the adsorbent-loaded channel.

As described above, the present invention makes it possible to provide a micro-fluidic cell for optical detection of gases, which can increase the sensitivity of optical detection of gases, selectivity of components, and accuracy of quantitative determination, and simultaneously achieve a low electric power consumption of the entire apparatus. The micro-fluidic cell for optical detection of gases according to the present invention also achieves a small-sized, light-weight configuration, and also permits analysis of gases in narrow regions as well as gas analysis with the passage of time. Furthermore, when a gas trapping cell usable with other measuring instruments is used in the micro-fluidic cell for optical detection of gases, more favorable effects are obtained.

The present invention has been described in detail with respect to preferred embodiments, and it will now be apparent from the foregoing to those skilled in the art that changes and modifications may be made without departing from the invention in its broader aspect, and it is the intention, therefore, in the apparent claims to cover all such changes and modifications as fall within the true spirit of the invention.

What is claimed is:

1. A micro-fluidic cell for optical detection of gases, comprising:
    a microchannel through which gases to be analyzed flow;
    a concentration cell; and
    a detection cell, and wherein
        said microchannel through which gases to be analyzed flow comprises a first microchannel including a gas inlet, a second microchannel including a gas outlet, and a connecting channel which connects said first microchannel and said second microchannel,
        said concentration cell comprising said first microchannel, a substance adapted to adsorb and desorb the gases to be analyzed, said substance being provided in at least a portion of said first microchannel, and a heating source for heating said substance for adsorbing and desorbing the gases to be analyzed, and
        said detection cell comprising said second microchannel, an optical fiber for entry of ultraviolet light for spectrophotometric analysis into said second microchannel, and an optical fiber for exit of the ultraviolet light for spectrophotometric analysis from said second microchannel.

2. A micro-fluidic cell for optical detection of gases as claimed in claim 1, wherein said concentration cell has a stopper for stopping said substance for adsorbing and desorbing the gases to be analyzed.

3. A micro-fluidic cell for optical detection of gases as claimed in claim 2, wherein said first microchannel has a microchannel for cold-trapping the gases to be analyzed which have been desorbed upon heating by said heating source.

4. A micro-fluidic cell for optical detection of gases as claimed in claim 3, wherein said first microchannel and said second microchannel are formed on different substrates, the substrates are stacked, and said connecting channel is a through-hole.

5. A micro-fluidic cell for optical detection of gases as claimed in claim 3, wherein said first microchannel, said second microchannel, and said connecting channels are formed on the same substrate.

6. A micro-fluidic cell for optical detection of gases as claimed in claim 3, wherein said microchannel for cold-trapping the gases to be analyzed is a channel free from a heater or a heat insulator and adapted to cool the gases by air cooling.

7. A micro-fluidic cell for optical detection of gases as claimed in claim 6, wherein a micro trench is provided in a top surface of the substrate corresponding to said microchannel for cold-trapping the gases to be analyzed.

8. A micro-fluidic cell for optical detection of gases as claimed in claim 7, wherein a cooling metallic thin film is provided in a bottom surface of the substrate corresponding to said microchannel for cold-trapping the gases to be analyzed.

9. A micro-fluidic cell for optical detection of gases as claimed in claim 6, wherein many micro pillars are provided in said microchannel for cold-trapping the gases to be analyzed.

10. A micro-fluidic cell for optical detection of gases as claimed in claim 9, wherein a cooling metallic thin film is provided in a bottom surface of the substrate corresponding to said microchannel for cold-trapping the gases to be analyzed.

11. A micro-fluidic cell for optical detection of gases as claimed in claim 1, wherein said first microchannel and said second microchannel are formed on different substrates, the substrates are stacked, and said connecting channel is a through-hole.

12. A micro-fluidic cell for optical detection of gases as claimed in claim 1, wherein said first microchannel, said second microchannel, and said connecting channel are formed on the same substrate.

13. A micro-fluidic cell for optical detection of gases as claimed in claim 1, wherein a tip of said optical fiber for entry is semispherical, and a tip of said optical fiber for exit is flat.

14. A micro-fluidic cell for optical detection of gases as claimed in claim 1, wherein a plurality of substances having different gas adsorbing and desorbing properties are used as said substance for adsorbing and desorbing the gases to be analyzed.

15. A micro-fluidic cell for optical detection of gases as claimed in claim 1, wherein said substance for adsorbing and desorbing the gases to be analyzed comprises at least one substance selected from the group consisting of porous glass, porous polymers, and porous carbon.

16. A gas trapping cell comprising:
    a microchannel having a gas inlet and a gas outlet port and permitting flow of gases to be analyzed;
    a substance provided in part of said microchannel and adapted to adsorb and desorb the gases to be analyzed;
    a heating source for heating said substance for adsorbing and desorbing the gases to be analyzed; and
    a microchannel for cold-trapping the gases to be analyzed which have been desorbed from said substance for adsorption and desorption provided in part of said microchannel.

17. A method for producing a micro-fluidic cell for optical detection of gases, comprising the steps of:
    forming a trench in a continuous pattern including an adsorbent stopper step on a top side of a first substrate;
    loading a substance for adsorbing and desorbing gases into part of the trench;
    connecting an optical fiber for entry of ultraviolet light for spectrophotometric analysis and an optical fiber for exit of the ultraviolet light for spectrophotometric analysis with a predetermined spacing in the trench by use of an sealing material comprising glass;

bonding a second flat substrate to the top side of the first substrate by bonding to form a microchannel in the trench; and providing a heater on a bottom side of the first substrate and at a position corresponding to a portion loaded with the substance for adsorbing and desorbing the gases.

18. A method for producing a micro-fluidic cell for optical detection of gases as claimed in claim 17, wherein the microchannel includes an adsorbent-loaded channel and a cold-trap channel, with the adsorbent stopper step being interposed therebetween.

19. A method for producing a micro-fluidic cell for optical detection of gases as claimed in claim 18, further comprising a step of forming a micro trench on a surface of the second substrate opposite to a surface thereof facing the first substrate, and at a position corresponding to the cold-trap channel.

20. A method for producing a micro-fluidic cell for optical detection of gases as claimed in claim 18, further comprising a step of forming a cooling metallic thin film on the bottom side of the first substrate and at a position corresponding to the cold-trap channel.

21. A method for producing a micro-fluidic cell for optical detection of gases as claimed in claim 17, wherein said step of providing the heater is applied by a method selected from the group consisting of metal mask method, lift-off technique, plating, and ion milling.

22. A method for producing a micro-fluidic cell for optical detection of gases as claimed in claim 17, wherein said step of forming the continuous trench pattern is applied by a method selected from the group consisting of a method using a dicing saw, wet etching, dry etching, and sand blasting.

23. A method for producing a micro-fluidic cell for optical detection of gases, comprising the steps of:

forming a trench in a continuous pattern including an adsorbent stopper step on a top side of a first substrate;

loading a substance for adsorbing and desorbing gases into part of the trench;

forming a trench in a predetermined continuous pattern on a top side of a second substrate and a through-hole in the trench;

connecting an optical fiber for entry of ultraviolet light for spectrophotometric analysis and an optical fiber for exit of the ultraviolet light for spectrophotometric analysis with a predetermined spacing in the trench of the second substrate by use of an sealing material comprising glass;

bonding a third flat substrate to the top side of the second substrate by bonding to form a microchannel in the trench of the second substrate;

bonding a bottom side of the second substrate to the top side of the first substrate by bonding to form a microchannel in the trench of the first substrate; and providing a heater on a bottom side of the first substrate and at a position corresponding to a portion loaded with the substance for adsorbing and desorbing the gases.

24. A method for producing a micro-fluidic cell for optical detection of gases as claimed in claim 23, wherein the microchannel of the first substrate includes an adsorbent-loaded channel and a cold-trap channel, with the adsorbent stopper step being interposed therebetween.

25. A method for producing a micro-fluidic cell for optical detection of gases as claimed in claim 24, further comprising a step of forming a micro trench on the bottom side of the first substrate and at a position corresponding to the cold-trap channel.

26. A method for producing a micro-fluidic cell for optical detection of gases as claimed in claim 24, further comprising a step of forming a cooling metallic thin film on the bottom side of the first substrate and at a position corresponding to the cold-trap channel.

27. A method for producing a micro-fluidic cell for optical detection of gases as claimed in claim 23, wherein said step of providing the heater is applied by a method selected from the group consisting of metal mask method, lift-off technique, plating, and ion milling.

28. A method for producing a micro-fluidic cell for optical detection of gases as claimed in claim 23, wherein said step of forming the continuous trench pattern is applied by a method selected from the group consisting of a method using a dicing saw, wet etching, dry etching, and sand blasting.

29. A method for producing a micro-fluidic cell for optical detection of gases, comprising the steps of:

forming a trench in a continuous pattern including an adsorbent stopper step on a top side of a first substrate;

loading a substance for adsorbing and desorbing gases into part of the trench;

bonding a second flat substrate having a through-hole at a position corresponding to the trench of the first substrate to the top side of the first substrate by bonding to form a microchannel in the trench of the first substrate;

providing a heater on a bottom side of the first substrate and at a position corresponding to a portion loaded with the substance for adsorbing and desorbing the gases;

forming a trench in a predetermined continuous pattern on a top side of a third substrate and a through-hole in the trench;

connecting an optical fiber for entry of ultraviolet light for spectrophotometric analysis and an optical fiber for exit of the ultraviolet light for spectrophotometric analysis with a predetermined spacing in the trench of the third substrate by use of an sealing material comprising glass;

bonding a fourth flat substrate having a through-hole at a position corresponding to the trench of the third substrate to the top side of the third substrate by bonding to form a microchannel in the trench of the third substrate; and stacking a fifth substrate comprising a Teflon seal packing interposed between the second substrate and the third substrate and having a through-hole at a position corresponding to the through-hole of the second substrate and the through-hole of the fourth substrate.

30. A method for producing a micro-fluidic cell for optical detection of gases as claimed in claim 29, wherein the microchannel includes an adsorbent-loaded channel and a cold-trap channel, with the adsorbent stopper step being interposed therebetween.

31. A method for producing a micro-fluidic cell for optical detection of gases as claimed in claim 30, further comprising a step of forming a micro trench on the bottom side of the first substrate and at a position corresponding to the cold-trap channel.

32. A method for producing a micro-fluidic cell for optical detection of gases as claimed in claim 30, further comprising a step of forming a cooling metallic thin film on the bottom side of the first substrate and at a position corresponding to the cold-trap channel.

33. A method for producing a micro-fluidic cell for optical detection of gases as claimed in claim 29, wherein said step of providing the heater is applied by a method selected from the group consisting of metal mask method, lift-off technique, plating, and ion milling.

34. A method for producing a micro-fluidic cell for optical detection of gases as claimed in claim 29, wherein said step of forming the united trench pattern is applied by a method selected from the group consisting of a method using a dicing saw, wet etching, dry etching, and sand blasting.

35. An apparatus for optical detection of gases, comprising:
- a micro-fluidic cell for optical detection of gases, including a microchannel through which gases to be analyzed flow, a concentration cell, and a detection cell;
- a heater power source;
- an ultraviolet light source;
- an ultraviolet spectrophotometer; and
- a controller, and wherein
    said microchannel through which the gases to be analyzed flow comprises a first microchannel including a gas inlet, a second microchannel including a gas outlet, and a connecting channel which connects said first microchannel and said second microchannel;

said concentration cell comprising said first microchannel, a substance adapted to adsorb and desorb the gases to be analyzed, said substance being provided in at least a portion of said first microchannel, and a heating source for heating said substance for adsorbing and desorbing the gases to be analyzed, and said detection cell comprising said second microchannel, an optical fiber for entry of ultraviolet light for spectrophotometric analysis into said second microchannel, and an optical fiber for exit of the ultraviolet light for spectrophotometric analysis from said second microchannel.

* * * * *

UNITED STATES PATENT AND TRADEMARK OFFICE
CERTIFICATE OF CORRECTION

PATENT NO.   : 6,600,558 B2
DATED          : July 29, 2003
INVENTOR(S)  : Ueno et al.

It is certified that error appears in the above-identified patent and that said Letters Patent is hereby corrected as shown below:

Column 3,
Line 31, change "an" to -- a --.

Column 10,
Line 67, after "A" remove "of".

Column 13,
Line 23, change "The" to -- the --.

Column 24,
Line 66, change "an" to -- a --.

Column 25,
Line 47, change "an" to -- a --.

Column 26,
Line 39, change "an" to -- a --.

Signed and Sealed this

Twenty-seventh Day of September, 2005

JON W. DUDAS
*Director of the United States Patent and Trademark Office*